United States Patent [19]
Mitchell et al.

[11] Patent Number: 6,130,434
[45] Date of Patent: Oct. 10, 2000

[54] DISSOLUTION STAGE FOR AN ENVIRONMENTAL SCANNING ELECTRON MICROSCOPE

[75] Inventors: James A. Mitchell, Carmel, N.Y.; Philip J. Palermo, Bethel, Conn.

[73] Assignee: Euro-Celtique, S.A., Luxembourg, Luxembourg

[21] Appl. No.: 09/316,862

[22] Filed: May 21, 1999

Related U.S. Application Data

[60] Provisional application No. 60/086,427, May 22, 1998.

[51] Int. Cl.$^7$ .............................. H01J 37/00; H01J 37/26; H01J 37/252
[52] U.S. Cl. ................................. 250/441.11; 250/442.11; 250/440.11; 250/310; 250/306
[58] Field of Search ........................... 250/441.11, 442.11, 250/440.11, 306, 310; 359/398, 396

[56] References Cited

U.S. PATENT DOCUMENTS

| | | | |
|---|---|---|---|
| 5,750,989 | 5/1998 | Lindsay et al. | 250/306 |
| 5,753,814 | 5/1998 | Han et al. | 73/105 |

*Primary Examiner*—Bruce C. Anderson
*Assistant Examiner*—Nikita Wells
*Attorney, Agent, or Firm*—Davidson, Davidson & Kappel LLC

[57] ABSTRACT

A system is provided for imaging, in an ESE microscope or other variable pressure microscope, a single sample at various time intervals during dissolution of the sample in a liquid. The system includes a sample chamber having a sample well. The sample well includes an first fluid port and a second fluid port for forming a dissolution bath in the sample well. In accordance with the system according to the present invention, the sample chamber is placed into the specimen chamber of the ESE microscope and a sample is deposited into the sample well of the sample chamber. The sample is immersed in a liquid which flows through the sample well via the first and second fluid ports during a dissolution cycle. The liquid is then drained from the sample well via one of the first and second fluid ports during a draining cycle, and then, during an imaging cycle, the sample is imaged by the ESE microscope. The dissolution cycle, the draining cycle, and the imaging cycle all occur while the sample well is inside the specimen chamber of the ESE microscope.

23 Claims, 22 Drawing Sheets

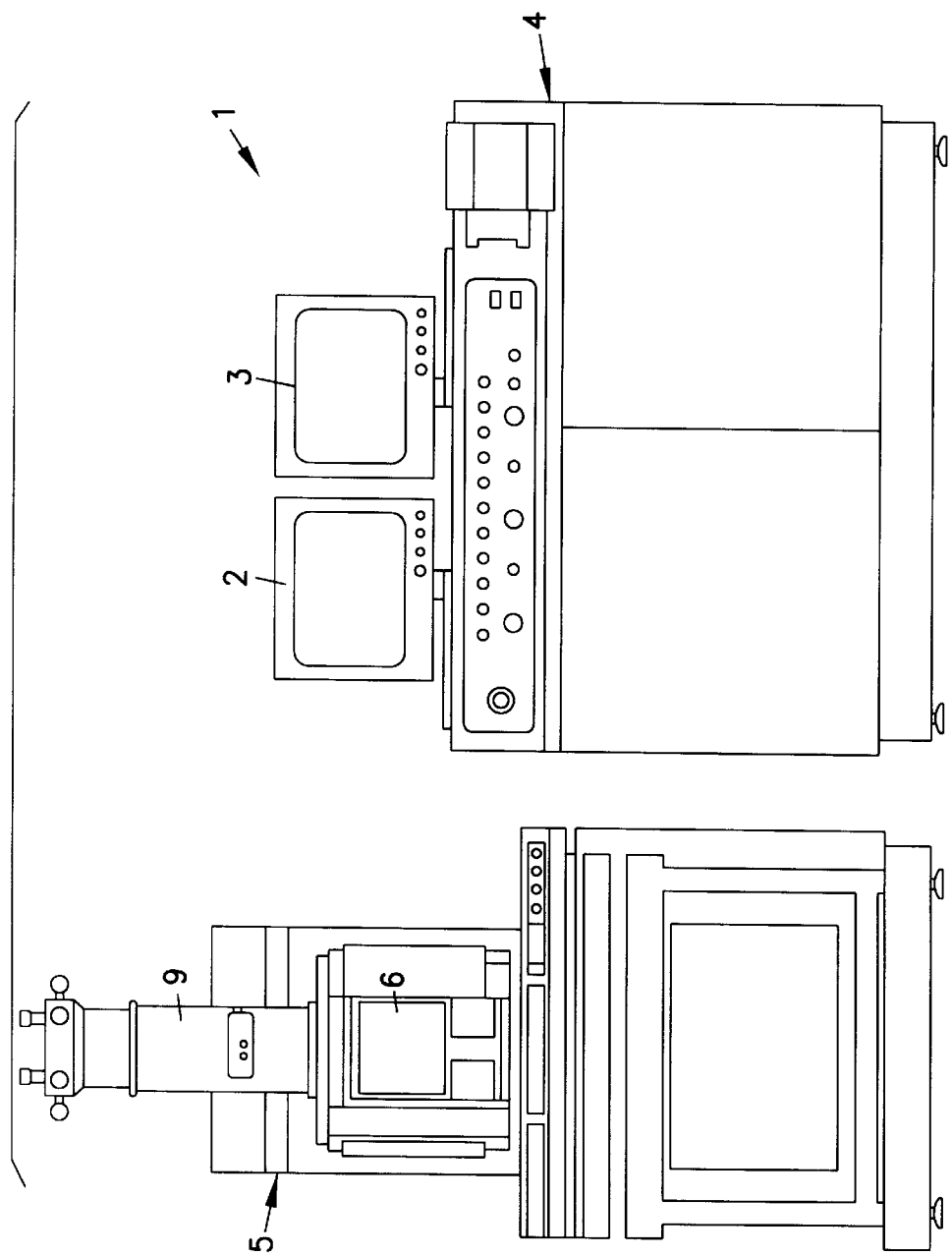

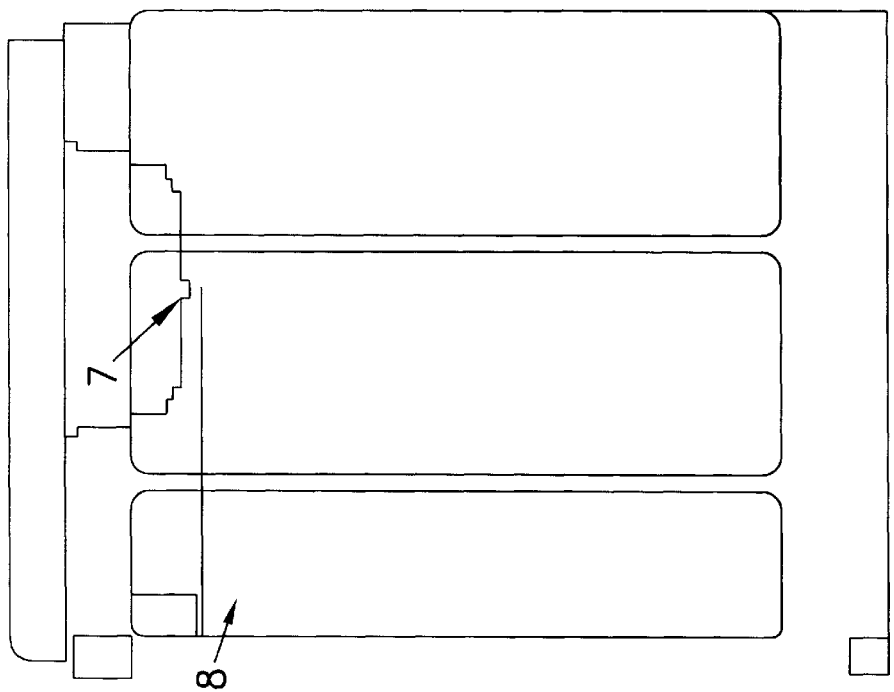
Fig. 2B
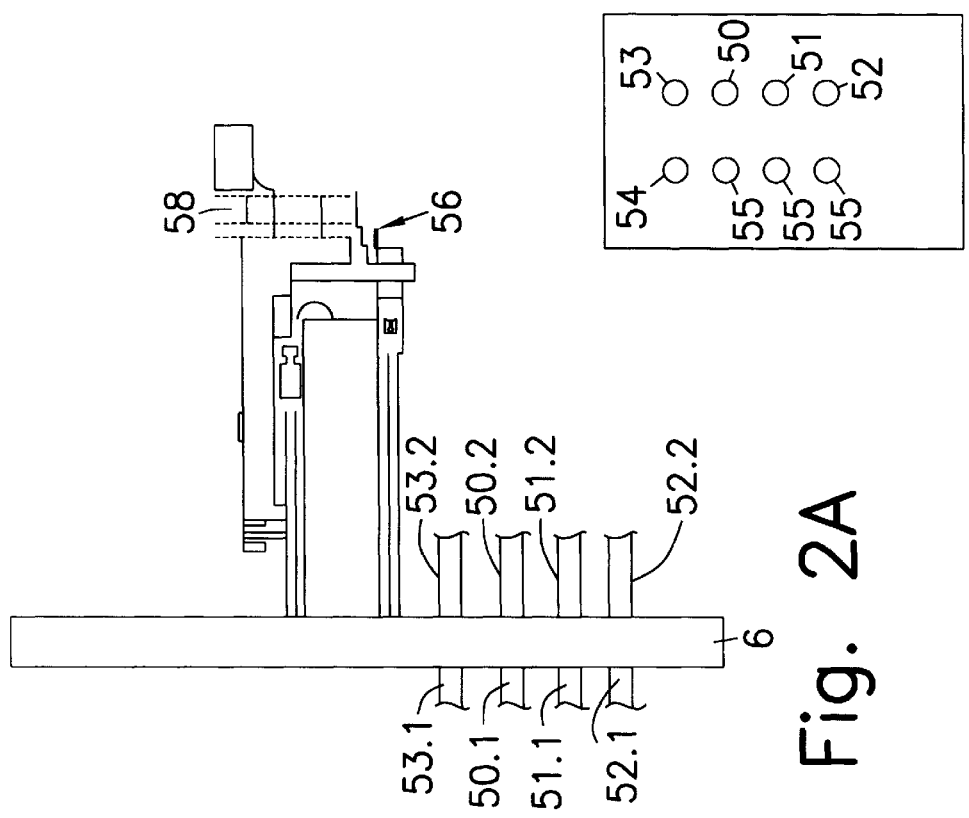
Fig. 2C
Fig. 2A

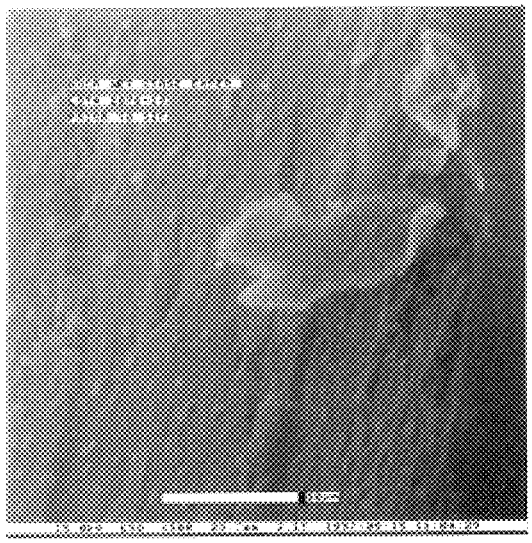 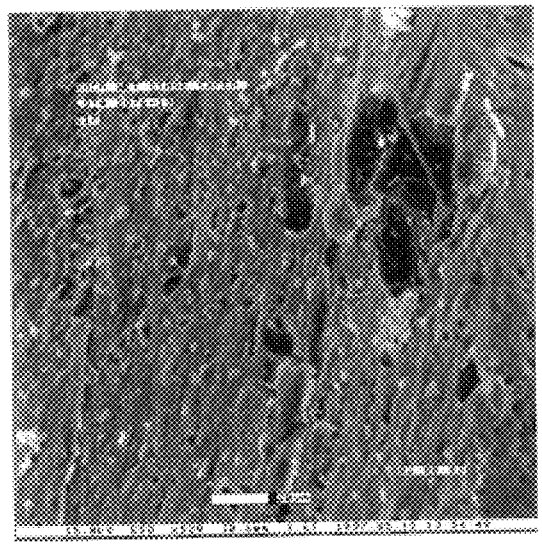
Fig. 16    Fig. 17
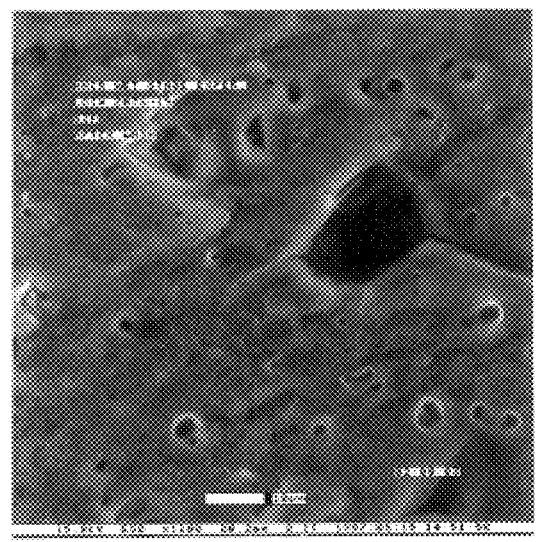
Fig. 18

DISSOLUTION STAGE FOR AN ENVIRONMENTAL SCANNING ELECTRON MICROSCOPE

This application claims priority from U.S. Provisional application Ser. No. 60/086,427, filed May 22, 1998, the entire disclosure of which is hereby incorporated by reference.

FIELD OF THE INVENTION

The present invention relates to the field of environmental scanning electron microscopes, and methods for using the same.

BACKGROUND OF THE INVENTION

Conventional Scanning Electron Microscopes (CSEMs) require most samples to be dried of all water, and then coated with metal or carbon. This treatment generally precludes the study of dynamic events, such as the effects of dissolution.

In contrast, Environmental Scanning Electron Microscopes (ESE microscopes) and similar variable pressure microscopes, allow samples with a high moisture content to be imaged. Within an ESE Microscope, the samples are imaged by introducing water vapor into the chamber, and ionizing the vapor cloud directly over the sample. By controlling both the chamber pressure and the sample temperature, the sample can be maintained in a water saturated state.

SUMMARY OF THE INVENTION

In order to evaluate the effect of a substance on a sample, it is desirable to view a single sample at various time intervals after being exposed to the substance in a dissolution bath. For example, the dissolution characteristics of controlled released pharmaceuticals are often critical to the pharmaceutical's usefulness. Moreover, it is often important to monitor the dissolution of controlled release pharmaceuticals for extended time periods (e.g. 8, 12, or 24 hours or more).

Since the controlled release pharmaceuticals are moist during dissolution, it is advantageous to view these pharmaceuticals using an ESE microscope or other variable pressure microscope. This approach, however, has a number of drawbacks. First, the controlled release pharmaceutical sample is subject to damage when it is transferred from the dissolution bath to the ESE microscope. Second, once a sample of the pharmaceutical is removed from the dissolution bath for viewing with the ESE microscope, it can not be returned to the dissolution bath.

To alleviate these problems, conventional ESE microscope's offer a "peltier stage" which is mounted in the ESE microscope specimen chamber and which allows moisture to be condensed onto a sample by controlling the temperature of the peltier stage. In this manner, the peltier stage can be used to provide a "dissolution bath" of water for a sample. The peltier stages, however, are inadequate for evaluating the dissolution characteristics of pharmaceuticals for a number of reasons.

For example, current peltier stages are too small to hold a pharmaceutical tablet and, since they operate by condensing moisture onto the sample from the atmosphere within the ESE microscope, they cannot provide the desired degree of "mixing" for an effective dissolution experiment. In addition, since they operate on a condensation principle, it is not possible to use these stages to conduct dissolution experiments with other dissolution media, such as simulated gastric fluid or simulated intestine fluid.

Moreover, in order to conduct a dissolution experiment with a peltier stage, the ESE microscope must first cool the stage so that enough water condenses into the sample well of the peltier stage to immerse the sample in water. Then, in order to image the sample, the stage must be heated sufficiently to evaporate the water in the well so that the sample can be imaged. This process has a number of disadvantages. First, rather than allowing the sample to be maintained at a desired temperature (for example, 98.6° F., 37° C.) throughout the experiment, the sample must be repeatedly cooled to cause condensation, and then heated to cause evaporation. As a result, it is not possible to simulate the dissolution environment of the human body. In addition, the condensation/evaporation technique becomes increasingly impractical as the size of the sample, and therefore the amount of water to be condensed and evaporated, is increased.

It is also known to deposit a sample into a sample cup located in the ESE microscope Specimen chamber, and to introduce liquid into a sample cup by using a syringe or similar device. Such a method, however, also fails to provide the desired degree of mixing, and, moreover, is inadequate for long term automated experiments because an operator must be present to refill the sample cup with liquid. Moreover, since this technique requires removal of the water by evaporation, it suffers from the same deficiencies as the peltier stage described above.

In accordance with the present invention, a system is provided for imaging, in an ESE microscope or other variable pressure microscope, a single sample at various time intervals during dissolution of the sample in a liquid. The system includes a sample chamber having a sample well. The sample well includes an first fluid port and a second fluid port for forming a dissolution bath in the sample well. In accordance with the system according to the present invention, the sample chamber is placed into the specimen chamber of the ESE microscope and a sample is deposited into the sample well of the sample chamber. Preferably, the sample well is large enough to fully immerse a typical pharmaceutical sample which is prepared as a solid oral dosage form (e.g. tablets from <5 mg to 1000 mg). The sample is immersed in a liquid which flows through the sample well via the first and second fluid ports during a dissolution cycle. The liquid is then drained from the sample well via one of the first and second fluid ports during a draining cycle, and then, during an imaging cycle, the sample is imaged by the ESE microscope. The dissolution cycle, the draining cycle, and the imaging cycle all occur while the sample well is inside the specimen chamber of the ESE microscope. By immersing the sample in a flowing liquid, a mixing effect is achieved which promotes dissolution of the sample because it reduces or eliminates the boundary zones which would otherwise form around the sample and impede dissolution. Moreover, since the sample well is filled and drained while it remains in the specimen chamber, a single sample can be imaged at various stages of dissolution by draining the well, imaging the sample, and then refilling the well at predetermined time intervals. In addition, the sample chamber in accordance with the present invention is not limited to using water as the dissolution fluid. Other dissolution media, such as simulated gastric fluid or simulated intestine fluid, can also be used.

Preferably, the second fluid port of the sample well is elevated relative to the first fluid port. This construction provides a number of additional advantages including i) preventing overflow of the well; and ii) providing a "sipping" effect which causes the level of water in the well to rise and fall, thereby enhancing the mixing effect. In accordance with this embodiment, the sample well is filled by coupling a source of dissolution fluid to the first fluid port during the dissolution cycle, and then coupling the first fluid port to a drain line during the draining cycle to drain the fluid from the sample well. A vacuum source (such as a pump) could also be coupled to the drain hose to more quickly and effectively drain the fluid from the sample well. This can be implemented in any known manner. For example, a three port valve could be used, with one port coupled to a water faucet, one port connected to a drain hose, and the other port connected to the first fluid port of the sample well. The valve could then be actuated in any known manner to couple the water faucet to the input port during the dissolution cycle, and to couple the drain hose to the first fluid port during the draining and imaging cycles. The valve could be actuated mechanically or electrically (or in any other known manner), and the actuation could be triggered manually by the operator, or automatically via, for example, a computer or other automatic control system.

In accordance with a further aspect of the invention, a passage at least partially surrounds the sample well, and the passage is coupled to a heating and/or cooling source to provide for temperature control of a sample placed in the sample well. Preferably, water is used as the heating and cooling medium. This construction provides excellent heat transfer characteristics and allows large samples to be quickly heated and cooled.

In accordance with another embodiment of the invention, the sample chamber includes a movable lid which covers the sample well during the dissolution cycle, and exposes the sample well during the imaging cycle in order to allow imaging of the sample. In general, an ESE microscope seeks to maintain the pressure in the specimen chamber at a specified level. If the sample well of the sample chamber is uncovered during the dissolution cycle, water will evaporate into the specimen chamber, and alter the pressure in the specimen chamber. Upon detecting the change in pressure, the ESE microscope will utilize its pumps to increase or decrease the pressure until specified pressure level is attained. This causes an undesirable strain on the pumps, which are not designed to compensate for the relatively large amount of water which evaporates during the dissolution cycle. Therefore, by providing a movable lid for the sample chamber, the strain on the ESE microscope's pumps is reduced. Alternatively, the microscope's vaccum pumps could be set to standby, eliminating the need to place a lid on the well.

In accordance with a still further embodiment of the invention, the system is configured to run long term automated dissolution experiments. In accordance with this embodiment, the system includes a controller, an ESE microscope, a sample chamber, and an image storage device. The image storage device and controller can be of any known construction. For example, the image storage device could be a VCR or a computer, and the controller could be a computer or even a simple programmable timer.

This construction allows an operator to perform in-chamber dissolution experiments with a variety of dissolution media, provides improved thermal control of larger samples, eliminates the mixing problems associated with prior art stage baths, allows for long running experiments (e.g., 8, 12, 24 hrs. or more) with increased automation, provides automatic image capture during long running experiments, and protects the ESE microscope from excessive amounts of moisture during non-imaging periods.

BRIEF DESCRIPTION OF THE DRAWINGS

FIG. 1 shows a prior art ESE microscope system including an ESE microscope, a control console, an image monitor, and control monitor.

FIG. 2 shows a microscope chamber door of the ESE microscope of FIG. 1.

FIG. 16 is a photograph of an unmoistened sample positioned at between 20 mm and 31 mm working distance, and imaged at magnification 500×(comparative).

FIG. 17 is a photograph of the sample of FIG. 16 after being immersed in a dissolution bath for 2 hours, and imaged at magnification 520×.

FIG. 18 is a photograph of the sample of FIG. 16 after being immersed in a dissolution bath for 2 hours, and imaged at magnification 1000×.

DETAILED DESCRIPTION OF THE PREFERRED EMBODIMENTS

Figure 3:
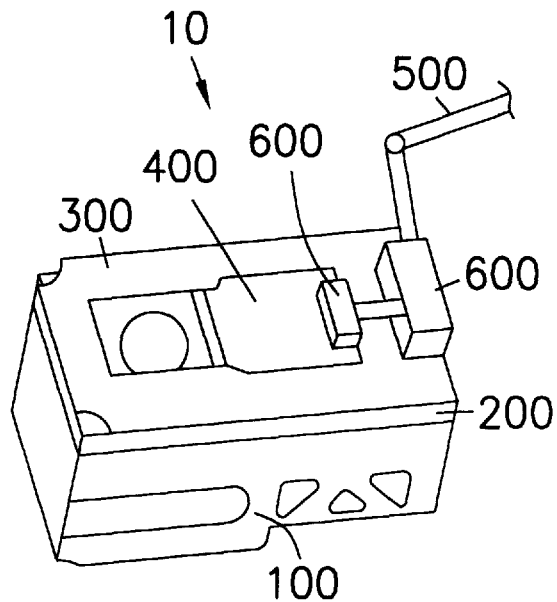
FIG. 3 shows a preferred embodiment of a sample chamber in accordance with the present invention.
Figure 4:
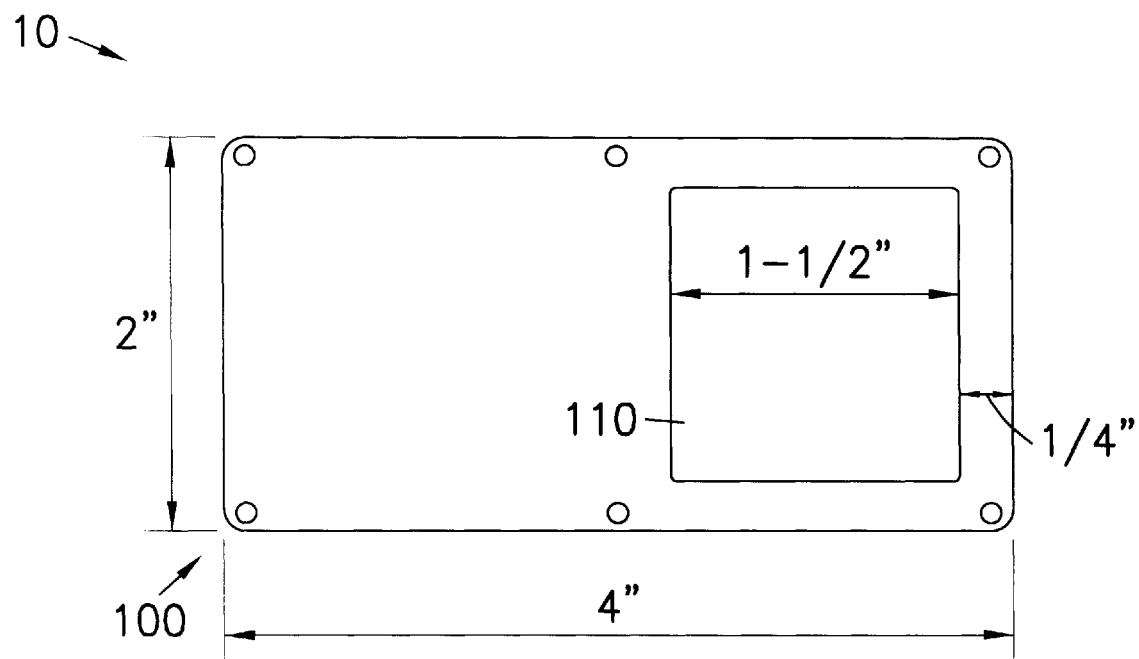
FIG. 4 shows a top view of a base of the sample chamber of FIG. 3.
Figure 5:
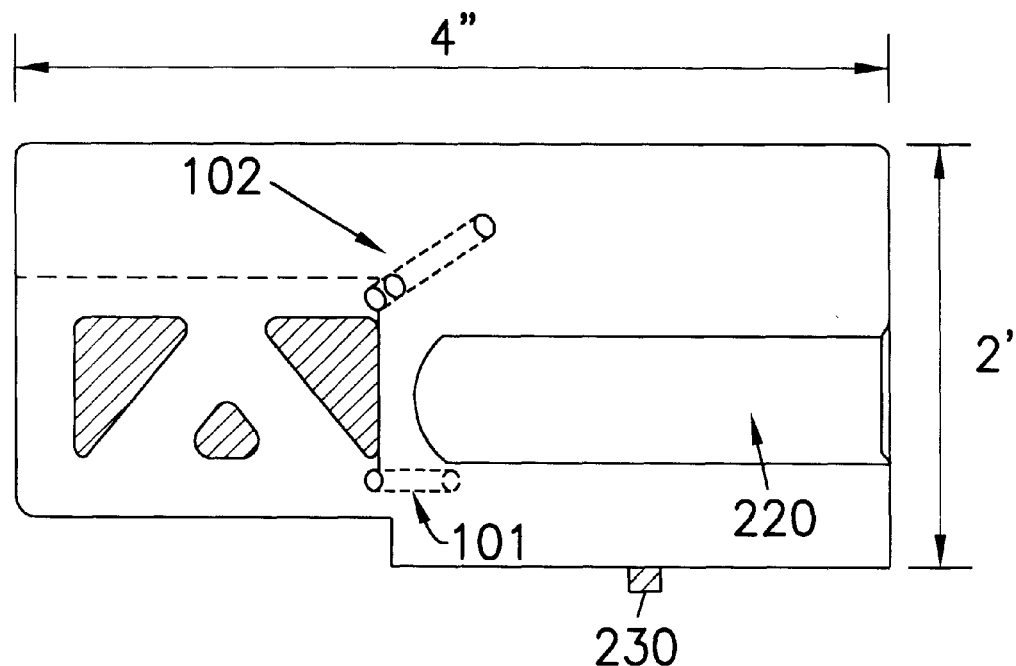
FIG. 5 shows a side view of the base of FIG. 4.
Figure 6:
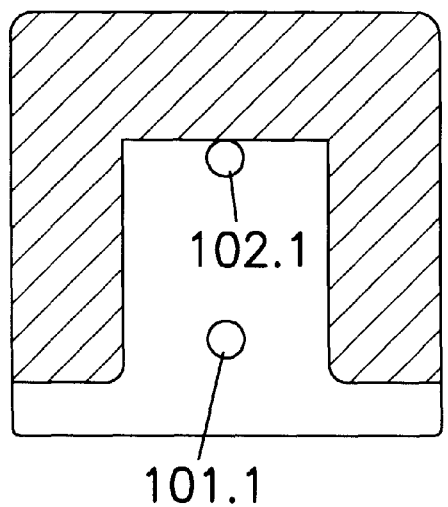
FIG. 6 shows a back view of the base of FIG. 4.
Figure 7:
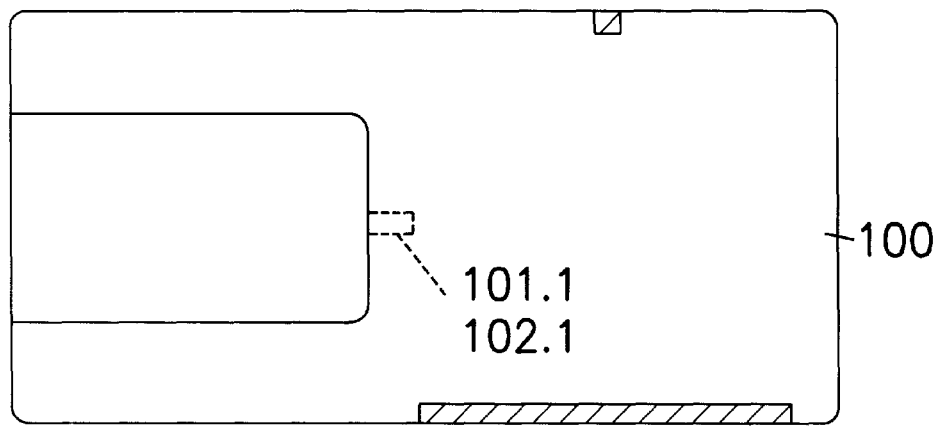
FIG. 7 shows a bottom view of the base of FIG. 4.

FIGS. 1 and 2 show a prior art ESE microscope system 1 including an ESE microscope 5, a control console 4, an image monitor 2, and a control monitor 3. As explained above, the ESE microscope system 1 allows samples with a high moisture content to be imaged. The ESE microscope 5 includes an electron gun 9, an environmental secondary detector 7, and a specimen chamber 8. The ESE microscope includes pumps and valves (not shown) which are operable to control the pressure within the specimen chamber 8. The electron gun 9 generates a beam of electrons which strike a specimen contained in the specimen chamber. The environmental secondary detector 7 uses principles of gas ionization to collect and amplify the picoampere-level imaging signals originating from the interaction between the electron beam and the specimen. The principles under which the ESE microscope system 1 operate are well known and therefore will not be discussed herein. It should be noted, moreover, that any known ESE microscope or variable pressure microscope system may be used in accordance with the present invention, including for example, ESE microscope systems manufactured by the ElectroScan Corporation, and described in U.S. Pat. Nos. 5,412,211, 5,362,964, 4,992,662, 4,842,006, and others.

FIG. 2 shows a microscope chamber door 6, environmental secondary detector 7, and specimen chamber 8 for the ESE microscope 5 of FIG. 1. The door 6 includes a platform 56, which is conventionally used to support a peltier stage or specimen holder. The door also includes a plurality of ports 50, 51, 52, 53, 54, 55. Ports 50 through 53 provide a coupling for respective hoses 50.1 th rough 53.1 and 50.2 through 53.2. Port 54 provides a rotational coupling for connection to drive shafts and the like. Ports 55 may provide connectivity for additional components such as probes and the like. Alternatively, port 54, or any of the other ports can be mounted through any of the chamber's walls.

FIG. 3 shows a sample chamber 10 in accordance with a preferred embodiment of the invention. The sample chamber 10 includes a base section 100, a middle section 200, a lid guide 300, a lid 400, a drive shaft 500, and drive mechanism 600. Referring to FIGS. 4 through 7, the base section 100 includes a cavity 110 which is configured to provide a water bath for controlling the temperature of a sample to be imaged by the ESE microscope. A bath fill passage 101 and a bath drain passage 102 each extend from the cavity to respective hose connections 101.1 and 102.1 on the exterior of the base 100. Hose connections 101.1 and 102.1 are coupled to ports 50 and 51 via hoses 50.2 and 51.2, respectively.

Figure 8:
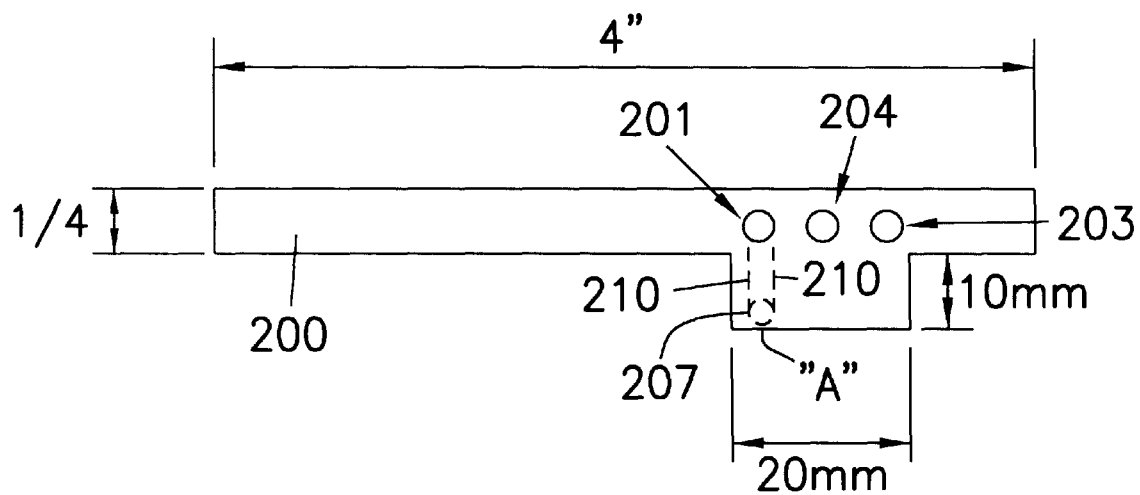
FIG. 8 shows a side view of a sample well of the sample chamber of FIG. 3.
Figure 9:
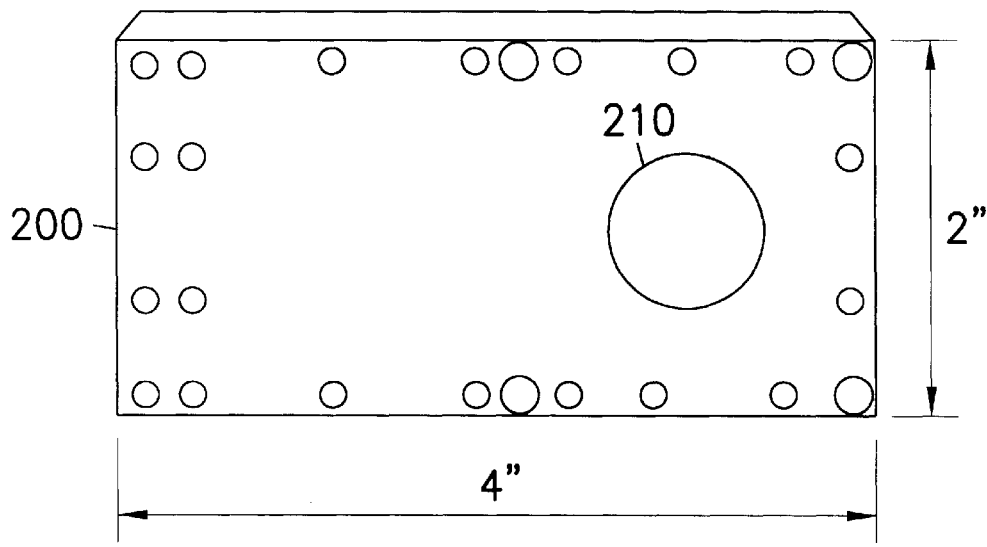
FIG. 9 shows a top view of the sample well of FIG. 8.

Referring to FIGS. 3, 8 and 9, the middle section 200 includes a sample well 210 for holding a sample to be imaged. The sample well 210 has a depth and width which are smaller than the depth and width of the cavity 110 so that a taurus is formed around the sample well when the middle section is mounted over the base section as shown in FIG. 3. Preferably, the sample well is large enough to fully immerse most oral solid dosage forms of pharmaceuticals. As an illustration, a sample well with a depth and diameter of 20 mm may be used. The middle section 200 includes a dissolution bath input port 201, a dissolution bath output port 203, and a probe input port 204. A passage 210 extends downward from the input port 201, and opens onto the interior surface of the sample well wall at 207. A second passage (not shown) extends from the output port 203 and opens onto the interior surface of the sample well wall, above the corresponding opening 207. A third passage (not shown) extends from the input port 204 and opens onto the interior surface of the sample well. Ports 201 and 203 are coupled to ports 52 and 53 via respective hoses 52.2 and 53.2. When desired, a probe can be inserted through port 204, and be connected to a respective monitoring device through one of the ports 55.

Figure 13:
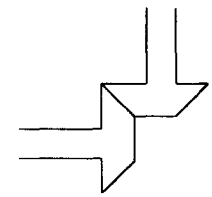
FIG. 13 shows an illustrative drive mechanism in accordance with the invention.
Figure 12:
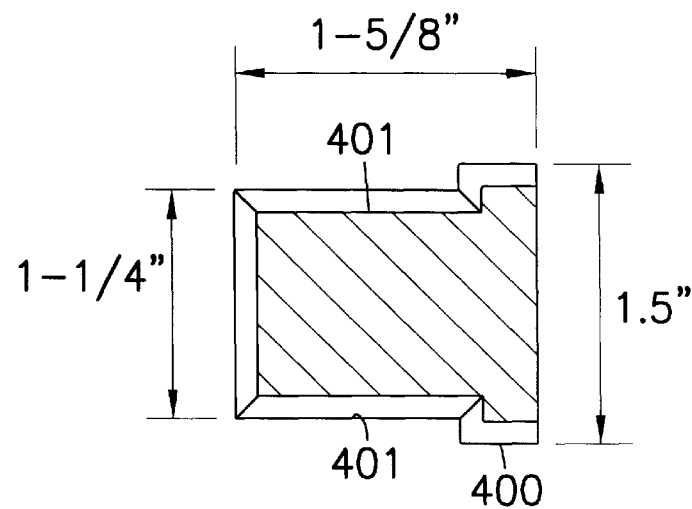
FIG. 12 shows a top view of a lid of the sample chamber of FIG. 3.
Figure 11:
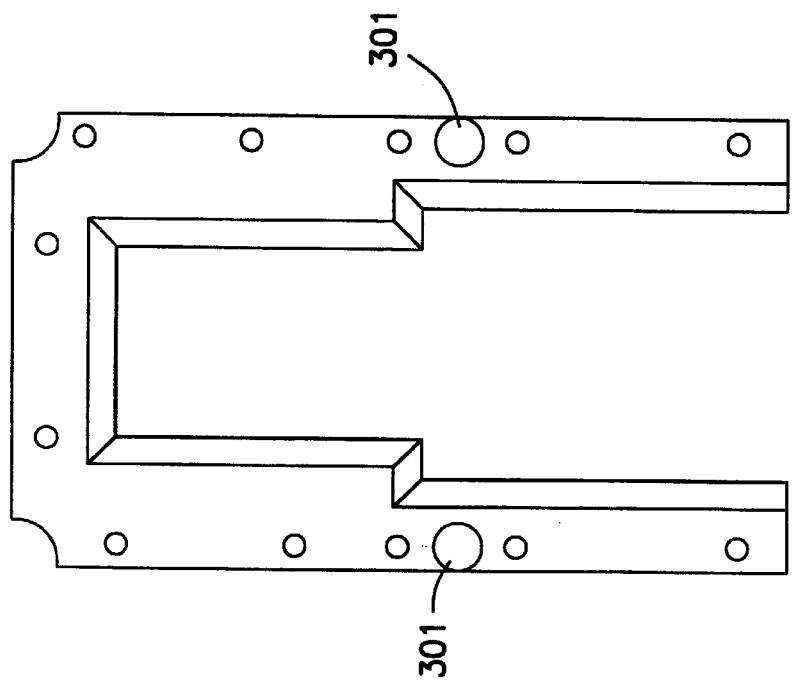
FIG. 11 shows a bottom view of the lid track of FIG. 10.
Figure 10:
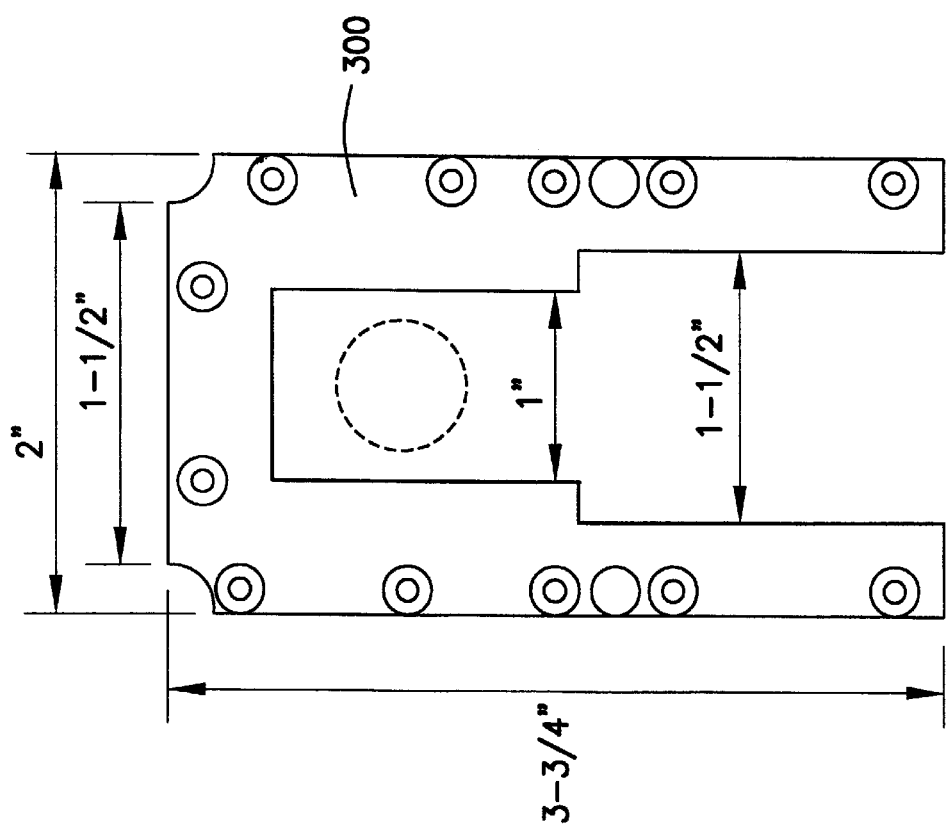
FIG. 10 shows a top view of a lid track of the sample chamber of FIG. 3.

Referring to FIGS. 3, 10, 11, and 12 a lid guide 300 is mounted over the middle section 200, and a lid 400 is disposed between the lid guide 300 and the middle section 200, such that the lid 400 can slide laterally over the middle section 200, to alternatively cover or expose the sample well 210. A gasket (not shown) may be used to provide a seal between the lid 400 and the sample well 210. The gasket could, for example, either be mounted to the lid 400 or be disposed around the sample well opening. Referring to FIGS. 10 through 12, the lid 400 and the lid guide 300, include beveled portions 401 and 301 which provide a secure fit between the lid 400 and the sample well 210 by pressing the lid 400 against the sample well, and compressing the gasket to form a seal, when the lid 400 is slid over the sample well. The movement of the lid 400 is controlled by the drive shaft 500 via the drive mechanism 600. While the drive mechanism 600 can be of any known construction, a simple rack and pinion arrangement, or a simple bevel gear arrangement, can be used. An exemplary bevel gear arrangement is shown in FIG. 13. The drive shaft 500 is coupled to rotational coupling 54.

The operation of the sample chamber 10 will now be described. The sample chamber 10 is mounted to the platform 56 of the microscope chamber door 6. The manner in which the chamber 10 is mounted to the platform 56 will depend on the structure of the platform of the ESE microscope 5 which is used. FIGS. 3–7 show a base 100 of the chamber 10 which is configured to be mounted to the platform 56 of an ElectroScan Model E-3, circa 1992. In this regard, grooves 220 are provided on the lateral sides of the base 100, for engagement to clamps (not shown) mounted to the platform 56. Moreover, a tab 230 is provided on the bottom side of the base 100, which is mounted in a corresponding notch 58 in the platform 56.

After the chamber 10 is secured to the platform 56, the hoses 50.2 through 53.2, and the shaft 500, are connected to respective ports 50 through 53, and 54 on the interior side of the door 6. Port 50 is connected from the exterior side of door 6 to a source of dissolution fluid such as water, simulated gastric fluid or simulated intestine fluid. Port 52 is connected from the exterior side of door 6 to a source of temperature controlled water, such as tap water which is passed through a conventional heat exchanger before being applied to port 52. Port 53, which forms part of the drain passage for the cavity 110, can either be connected to a drain or be recycled through the source of temperature controlled water. Port 51, which forms part of the drain passage for the sample well 210, can either be connected to a drain or to an input of the source of dissolution fluid. Port 54 is coupled to a motor 700 (FIG. 14), such as a stepper motor. Once the sample chamber 10 has been configured in this manner, a sample, such a pharmaceutical tablet, is placed in the sample well, the door 6 of the ESE microscope 5 is closed, and the lid 400 is slid over the sample well 210 under the control of the motor 700.

A temperature controlled dissolution bath can then be created in the sample chamber in the following manner. The sample well is filled with dissolution fluid by applying the dissolution fluid from the source of dissolution fluid to the sample well via the passage formed by port 50, hose 50.2, port 201, passage 210, and opening 207. Once the level of fluid in the sample well reaches the port 203, the fluid will exit the sample well via port 203, passing through hose 51.2 and port 51 before reaching the drain or being recycled by the dissolution fluid source. By applying the fluid at the bottom of the sample well 210 and draining the fluid from the top of the sample well 210, this construction causes a mixing effect in the sample well 210 which reduces the boundary zones which would otherwise form around the sample in a stagnant fluid or a fluid which is filled from the top and drained from the bottom. Moreover, the "sipping" or "pulsing" effect caused by the level of the fluid bath in the sample well 210 oscillating between the top and bottom of the opening 203 further promotes mixing of the fluid in the sample well. The temperature of the fluid bath in the sample well 210 is controlled by the source of temperature controlled water. Water which has been heated or cooled to a selected temperature is fed into the cavity 110 via port 52, hose 53.2, and port 102.1, and then drained from the cavity 110 via port 102.2, hose 53.2, and port 53. In this manner, the temperature of the fluid bath in the sample well is quickly brought to the selected temperature by conduction from the water in the cavity 110 through the walls of the sample well 210. Moreover, a temperature probe can be installed via one of the ports 55 in order to directly monitor the temperature of the dissolution bath. Alternatively, the sample chamber temperature can be maintained by heating or cooling the dissolution liquid introduced to the sample well by ports 50 and 51.

After the sample has been submerged in the dissolution fluid for the time period desired by the operator, the source of dissolution fluid is decoupled from port 50, and a vacuum is applied to port 50 to drain the dissolution fluid from the sample well 210. Alternatively, the pump supplying fluid through port 50 could be reversed without decoupling the port. Once the fluid has been drained, the motor is engaged to slide the lid 400 into its open position, thereby exposing the sample to the specimen chamber of the ESE microscope 5. The ESE microscope 5 is then operated in a conventional manner to image the sample. After imaging, the lid 400 can be returned to its closed position (covering the sample well), the source of dissolution fluid re-coupled to port 50, and the sample well 210 filled with dissolution fluid in order to continue dissolution of the sample. This entire procedure can then be repeated at predetermined time intervals in order to obtain images of a single sample at different stages of dissolution.

Figure 15:
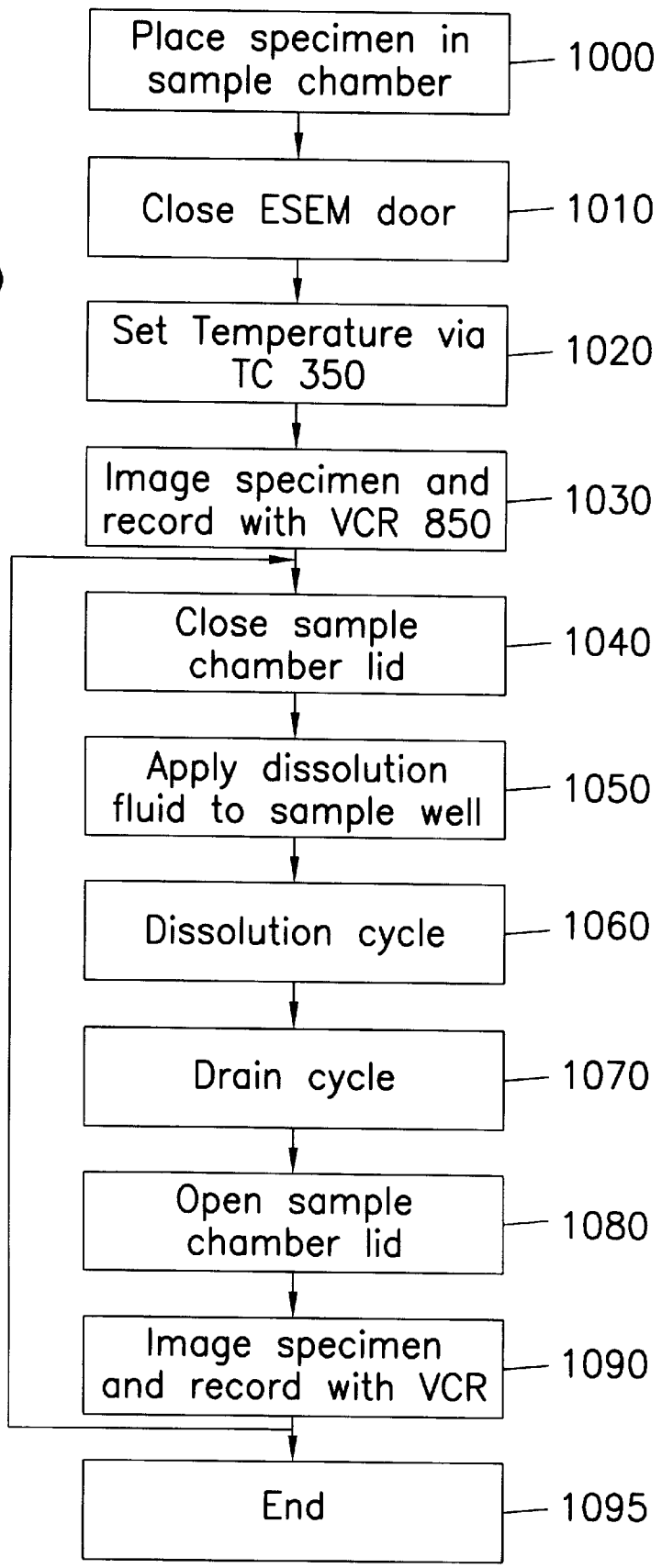
FIG. 15 shows a flow chart for conducting an automated experiment with the ESE microscope system of FIG. 14.

In accordance with a further embodiment of the invention, an automated system for imaging a single sample at selected time intervals during a dissolution experiment is provided. Referring to FIG. 15, the system includes an ESE microscope system 1 and sample chamber 10 as described above, and further includes an image storage device such as VCR 850 for recording the images generated by the ESE microscope 1. A source of dissolution fluid (SDF) 150 and a vacuum source (VAC) 250 are selectively coupled to port 50 of the ESE microscope 1 via a selective coupling device such as three way valve 450 (DFV). A temperature control device (TC) 350 such as heat exchanger is coupled to port 52. Preferably, a selective coupling device such as a two way valve 550 (TCV) is coupled between the temperature control device 350 and port 52 so that the supply of water can be cut off from the sample chamber. A motor 750 is coupled to port 54 in order to drive the drive shaft 500.

Figure 14:
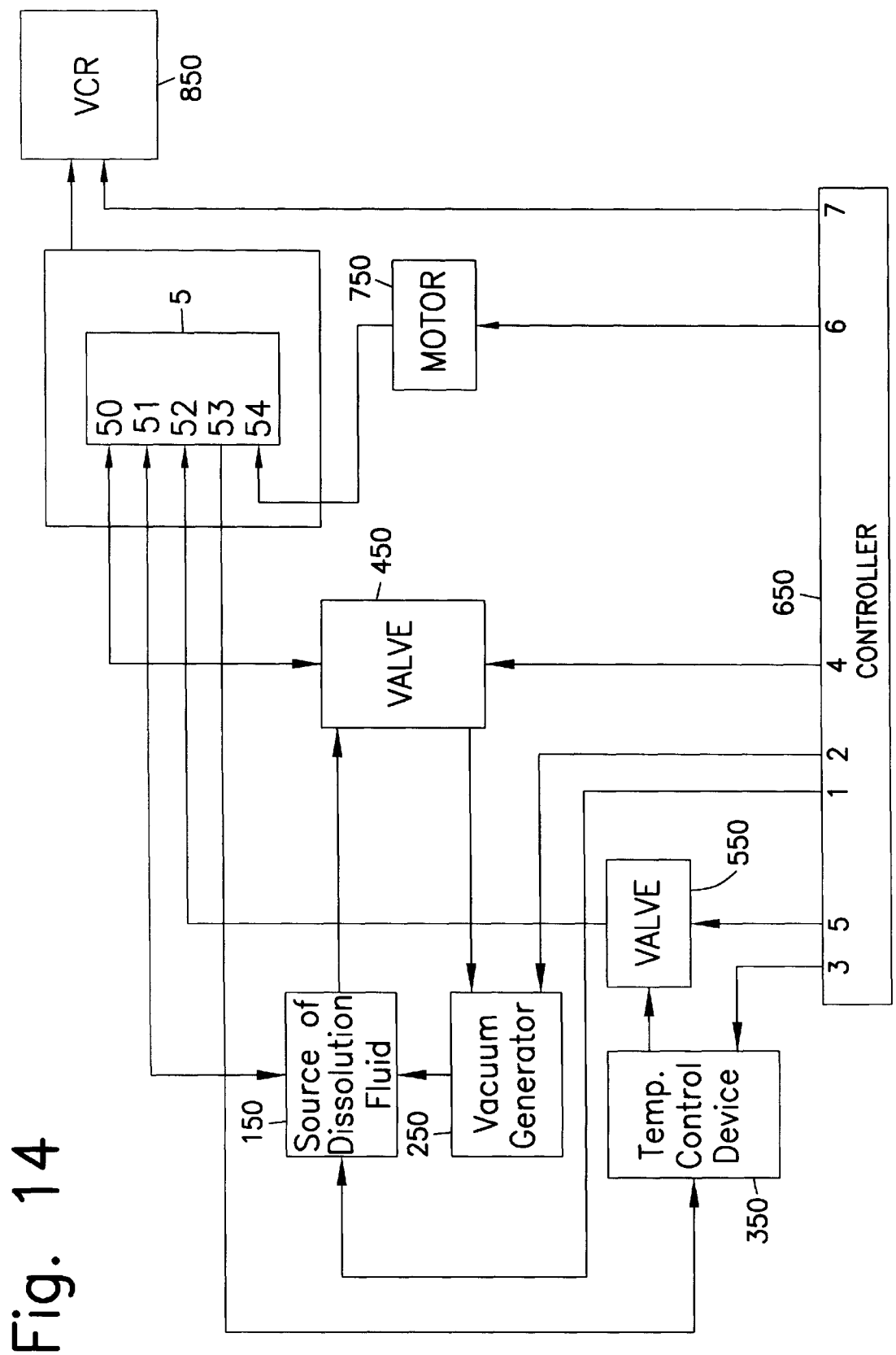
FIG. 14 shows an automated ESE microscope system in accordance with another embodiment of the invention.

In the embodiment illustrated in FIG. 14, the dissolution fluid drained from the sample well is recycled by coupling port 51 to an input port 151 of the source of dissolution fluid 150, and the water drained from the cavity 110 is recycled by coupling port 53 to an input of temperature control device 350. Recycling the water (and/or dissolution fluid) from the cavity 110 (and/or sample well) provides the advantage of conserving water (and/or dissolution fluid), and in addition, conserving energy because the fluid drained from the cavity 110 (and/or sample well) will generally be closer to the desired temperature than tap water. Recycling the fluid from the SDF 150 also serves as a safety feature. Specifically, since the total amount of dissolution fluid is limited, a leak or other failure is less likely to damage the microscope 1.

Recirculating the dissolution fluid also provides the advantage of more closely resembling conventional dissolution baths (and bodily conditions) by continuously dissolving the sample in a single volume of dissolution fluid rather than continuously introducing fresh fluid into the system. This allows the user to withdraw samples of the dissolution fluid from the SDF 150 at various stages of a dissolution experiment in order to analyze the substances which have been dissolved into the fluid (such as drugs, diluents, etc.). Moreover, since the amount of dissolved substances in the fluid will increase as the dissolution experiment continues, additional chemical analyses can be conducted which are difficult or impossible to conduct with smaller amounts of the dissolved substances.

The vacuum 250, the source of dissolution fluid 150, the temperature control device 350, the selective couplings 450, 550, and the motor 750 are controlled by a controller 650 via controller outputs 1 through 6. The controller 650 can be, for example, a computer, a programmable timer, a processor, a sequencer or other known control device. The VCR 850 can either be triggered by its own internal clock, or be triggered by the controller 650 via controller output 7 as shown in FIG. 14.

The manner in which the automated system of FIG. 14 operates will be explained by reference to the flow chart of FIG. 15, and by reference to the following example, in which a user wishes to monitor the dissolution of a pharmaceutical tablet at 4 hour intervals over a 24 hour time period. The controller 650, is programmed to actuate components 150, 250, 350, 450, 550, 750, and 850 by selectively applying a trigger signal on its respective outputs as follows, wherein "high" indicates an high voltage (e.g. 5 volts) and "low" indicates a lower voltage (e.g. 0 volts):

TABLE 1

|  | 1(SDF) | 2(VAC) | 3 (TC) | 4(DFV) | 5(TCV) | 6(MOTOR) | 7(VCR) |
| --- | --- | --- | --- | --- | --- | --- | --- |
| 0 hr. | Low | Low | High | Low | High | High | High |
| 0+ | Low | Low | High | Low | High | Low | Low |
| 0++ | High | Low | High | High | High | Low | Low |
| 4 hr. | Low | High | High | Low | High | High | Low |
| 4+ | Low | High | High | Low | High | High | High |
| 4++ | Low | High | High | Low | High | Low | Low |
| 4+++ | High | Low | High | High | High | Low | Low |

TABLE 1-continued

| | 1(SDF) | 2(VAC) | 3(TC) | 4(DFV) | 5(TCV) | 6(MOTOR) | 7(VCR) |
|---|---|---|---|---|---|---|---|
| 8 hr. | Low | High | High | Low | High | High | Low |
| 8+ | Low | High | High | Low | High | High | High |
| 8++ | Low | High | High | Low | High | Low | Low |
| 8+++ | High | Low | High | High | High | Low | Low |
| 12 hr. | Low | High | High | Low | High | High | Low |
| 12+ | Low | High | High | Low | High | High | High |
| 12++ | Low | High | High | Low | High | Low | Low |
| 12+++ | High | Low | High | High | High | Low | Low |
| 16 hr. | Low | High | High | Low | High | High | Low |
| 16+ | Low | High | High | Low | High | High | High |
| 16++ | Low | High | High | Low | High | Low | Low |
| 16+++ | High | Low | High | High | High | Low | Low |
| 20 hr. | Low | High | High | Low | High | High | Low |
| 20+ | Low | High | High | Low | High | High | High |
| 20++ | Low | High | High | Low | High | Low | Low |
| 20+++ | High | Low | High | High | High | Low | Low |
| 24 hr. | Low | High | High | Low | High | High | Low |
| 24+ | Low | High | High | Low | High | High | High |
| 24++ | Low | High | High | Low | High | Low | Low |
| 24+++ | High | Low | High | High | High | Low | Low |
| 24++++ | Low | Low | Low | Low | High | High | Low |

In accordance with this illustration, components 150, 250, 350, 850 are activated by a "high" voltage, and deactivated by a "low" voltage. Valve 450 connects SDF 150 to the ESE microscope 5 when a "high" voltage is applied, and connects VAC 250 to the ESE microscope 5 when a "low" voltage is applied. Valve 550 is open when a "high" voltage is applied, and is closed when a "low" voltage is applied. A "low" voltage applied to the motor 750 causes the lid 400 to close, and a "high" voltage applied to the motor 750 causes the lid 400 to open.

Referring to FIG. 15, at the beginning of an experiment, a specimen, such as a pharmaceutical tablet, is placed in the sample chamber 10 (step 1000), the ESE microscope door 6 is closed (step 1010), and the temperature of the fluid in the temperature controller 350 is set (step 1020). The remainder of the illustrative experiment will now be described with reference to Table 1 and FIG. 15.

At time "0 Hr.", an initial image of the sample is taken (step 1030) with the outputs of controller 650 set as follows: i) output 3=high (TC 350 is on); ii) output 5=high (the valve 550 is open, allowing the water from TC 350 to flow through the sample chamber 10), output 6=high (the lid 400 is open), and output 7 is high (the VCR is turned on). In the illustration of Table 1, the SDF 150 and the VAC 250 are turned off when not in use in order to conserve energy. It should be noted, however, the SDF 150 and VAC 250 may remain turned on throughout the entire experiment.

At time 0+ (and step 1040 of FIG. 15), output 6 is low (causing the lid 400 to close) and output 7 is high (turning the VCR off). In Table 1, the nomenclature [hour]+, [hour]++ etc. is used to indicate a sequence of events that occurs at the designated hour in the sequence [hour], [hour]+, [hour]++, [hour]+++, etc. In this regard, the specific time at which each event occurs is unimportant, so long as the indicated sequence is maintained.

At time 0++ (and step 1050 of FIG. 15), outputs 1 and 4 are high, turning on SDF 150, causing the valve 450 to connect SDF 150 to the sample chamber 10, and thereby causing the fluid from SDF 150 to circulate through the sample well 210.

At this point, the dissolution cycle (step 1060 of FIG. 15) commences and the tablet in the sample well undergoes dissolution from time=0++ to time=4 Hr.

At time=4 hr. (and step 1070), output 2 is high (turning on VAC 250) and output 4 is low. Consequently, the valve 450 connects the vacuum 250 to the sample chamber 10, and the fluid is drained from the sample well 210. In addition, output 6 is High, causing the motor 750 to open the lid 400 (step 1080). At time 4+, output 7 is high, causing the VCR to image the tablet in the sample well (step 1090).

At time 4++ (and step 1040 of FIG. 15), output 6 is low (causing the lid 400 to close) and output 7 is high (turning the VCR off). Then, at time 4+++ (and step 1050 of FIG. 15), output 4 is high causing the valve 450 to connect the SDF 150 to the sample chamber 10, and thereby causing the fluid from the SDF 150 to circulate through the sample well 210. At this point, the dissolution cycle (step 1060 of FIG. 15) commences and the tablet in the sample well undergoes dissolution from time=4+++ to time=8 Hr. This process is then repeated as indicated in Table 1 and FIG. 15 until images of the tablet are obtained at 4 hour intervals over a 24 hour period.

The controller 650 and valves 450, 550 are preferably located outside of the specimen chamber 8 in order to reduce the effect of electromagnetic fields on the electron beam of the ESE microscope. Only the hoses 50.2, 51.2, 52.2, 53.2, the drive shaft 500, and the sample chamber 10 reside in the specimen chamber 8. Moreover, the chamber 10 and drive shaft are preferably made of a non-magnetic material in order to prevent a magnetic field from developing. For example, the chamber 10 can be made of aluminum and the shaft and hose couplings made of brass or other suitable non-magnetic material. In addition, the construction of FIG. 14, with its external controls, allows the controls for the sample chamber 10 to be designed independent of the ESE microscope's operating system.

In accordance with a further embodiment of the present invention, a washing process, including a wash fill cycle and a wash drain cycle, is performed prior to the steps of opening the lid (1070) and imaging (1080). During the wash fill cycle, the sample well 210 is filled with water. Then, during the wash drain cycle, the sample well is drained of water in order to remove deposits (of for example, salt) which have formed on the sample during the preceding dissolution cycle 1060. By removing the deposits, only the sample, and not the sample and the deposits, will be imaged during the imaging step (1090). This process is particularly advantageous when simulated intestine fluid or simulated gastric fluid is used as the dissolution fluid, because these fluids tend to leave salt deposits on samples.

Figure 19:
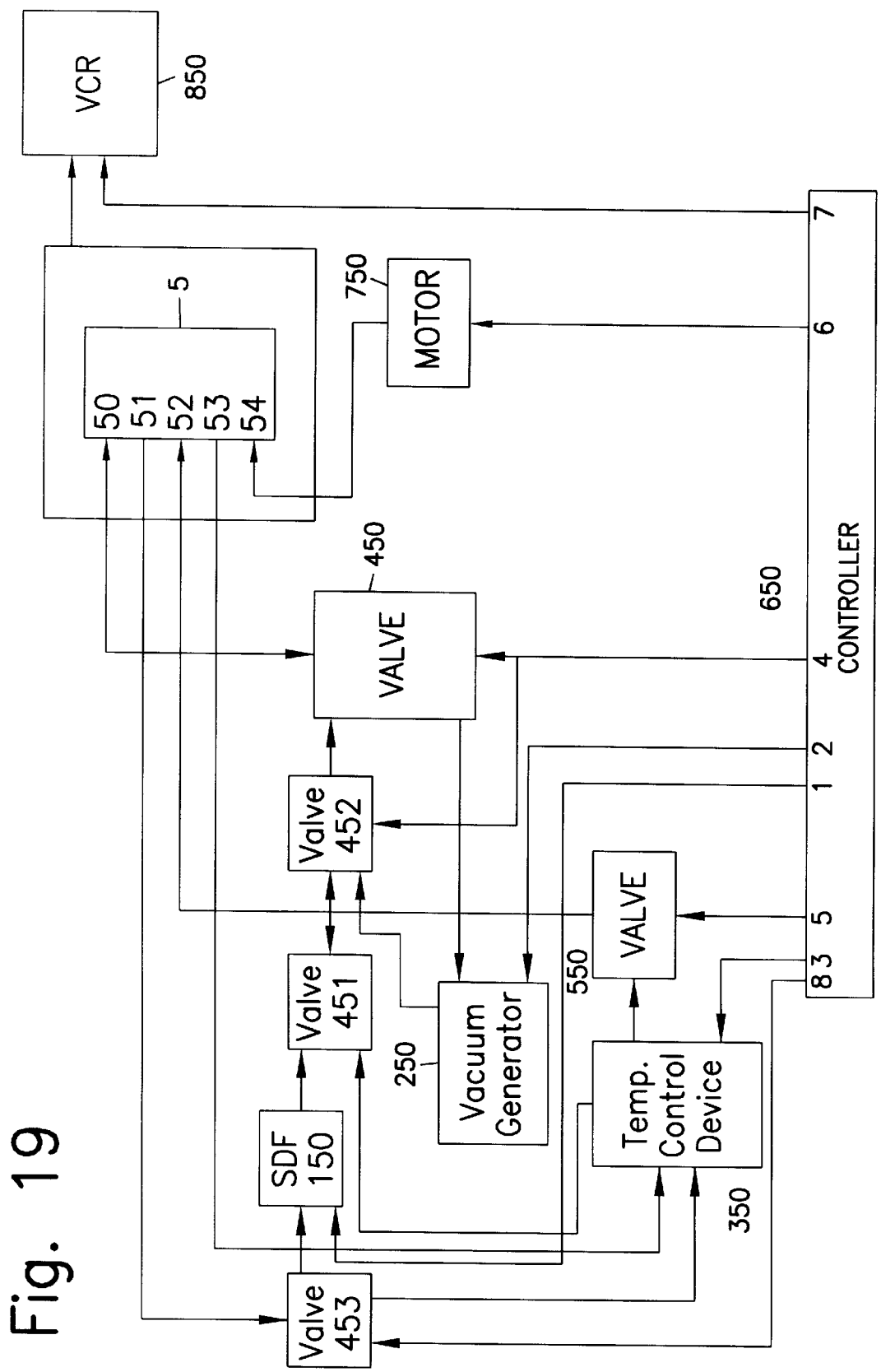
FIG. 19 is an automated ESE microscope system in accordance with a further embodiment of the invention.

FIG. 19 shows an illustrative control system which is configured to perform a washing process. The control system is identical to the control system of FIG. 14, except that the control system of FIG. 19 includes an additional control line 8 from the controller 650, and additional valves 451, 452, 453.

Since the control system of FIG. 19 is, in most respects, identical to the control system of FIG. 14, only the components and process steps of the control system of FIG. 19 which are different than the system of FIG. 14 will be discussed herein.

During the dissolution fluid filling cycle (step 1050, FIG. 15), a "HIGH" signal from control line 8 causes valve 451 to couple the SDF 150 to the valve 452. Since valve 452 is controlled by control line 4 (as shown in FIG. 19), a "HIGH" signal is applied to valve 452 during step 1050 (see Table 1 and corresponding discussion), coupling the fluid from SDF 150 through to port 50 via valves 452 and 450 in order to fill the sample well 210 with fluid. Valve 453, which is also controlled by control line 8, couples port 51 through to the SDF 150, thereby recycling the fluid from the dissolution bath output port 203 through to the SDF 150.

During the dissolution fluid draining cycle (step 1070, FIG. 15), a "LOW" signal is applied to the valves 450, 452, and the port 50 is coupled through valve 450, vacuum generator 250, valve 452, and valve 451 (which is still "HIGH") and into the SDF 150 so that the sample well 210 is drained of fluid.

During the "wash fill cycle" (which occurs after step 1070 and before step 1080 of FIG. 15), a "HIGH" signal is applied to valves 450, 452 via control line 4, and a "LOW" signal is applied to valves 451, 453 via control line 8. This causes the TC 350 (which in this embodiment is a self-contained recycling source of temperature controlled water, but could alternatively be a separate source of rinse water) to be coupled to the port 50 via valves 451, 452, 450, thereby filling the sample well 210 with water. The dissolution bath drain line 203 is coupled through the port 51 and valve 453 to the TC 350 so that the water is circulated through the sample well 210. Then, during the "wash drain cycle," a "LOW" signal is applied to valves 450, 452, via control line 4, and a "LOW" signal is applied to valves 451, 453 via control line 8. In this manner, port 50 is connected through valve 450, vacuum generator 250, valve 452, and valve 451 to TC 350, and the sample well 210 is drained of water, removing the deposits from the sample in the sample well 210. The system then proceeds to step 1080 of FIG. 15 and operates in the manner described above with regard to FIGS. 14 and 15.

In accordance with the embodiment of the sample chamber 10 illustrated in FIG. 3, a lid is provided to cover the sample well during the dissolution periods. This reduces the demands on the microscope's pumps, and protects both the sample well environment and the microscope environment during the non-imaging stages of the experiment. It is possible, however, to eliminate the lid of the sample chamber, and use a permanently open sample well. In such an embodiment, the ESE microscope's pumps would be required to handle the excess water evaporating off of the sample.

The sample chamber in accordance with the present invention, provides a number of additional advantages. It provides vastly improved image quality and sample stability even at the relatively long working distances required for this type of stage. It further provides the ability to observe samples at various stages of dissolution, the ability to introduce liquids to a sample in the chamber in either recirculation mode, or in flow through mode, the ability to return to the same region of a individual specimen repeatedly during various stages of dissolution, and the ability to sample directly from the sample well or from the drain line during dissolution for purposes of chemical analysis.

EXAMPLES 1 THROUGH 4

Improved Image Quality and Sample Stability

EXAMPLE 1

A drug loaded melt extruded pellet was mounted with the aid of mounting cement to a mounting stub, and the mounting stub and pellet were placed in a dissolution stage in accordance with FIGS. 3–12. The ESE microscope 5 is an ElectroScan Model E-3, the controller 650 is a 5 Amp min-step indexer drive for controlling the motor 650, and an Artisan programmable controller/timer model no. 4696 for controlling the remaining components. The SDF 150 is a container of simulated intestinal fluid pumped via a Masterflex pump model no. 1523-10, the VAC 250 is a Masterflex pump model no. 5762-10, the VCR 850 is a Hitachi time lapse VCR Model TL 2000, the TC 350 is an external water bath/circulator ALUDA model RMS E45028, the motor 650 is a NEMA 34 stepper motor, and the valves 450, 550 are conventional electronically controlled three-way valves. The controller/timer actuates components 150, 250, 350, 450, 550, 750, 850 by applying or removing 110 Volts AC on its outputs.

The sample is positioned at between 20 mm and 31 mm working distance, and imaged at magnification 500×, as shown in FIG. 16. Simulated Intestinal Fluid (SIF) was then introduced at a rate of approximately 20 ml per minute to the bath. After 1 hour, the SIF was drained and a wash bath was applied to remove salt deposits. SIF was then reintroduced to the sample well, and, after two hours of dissolution, the well was drained and the same point on the pellet surface was imaged at magnification 520×, and at magnification 1000×. The image quality obtained after the pellet was submerged in the dissolution bath (FIGS. 17 and 18) was found to be surprisingly superior than the image quality prior to dissolution (FIG. 16).

The relatively long working distance used in this experiment is desirable to prevent contamination of the secondary detector 7 from splattering of liquids from the sample well, to allow sufficient space for the sample well lid 400, and to provide improved depth of field during imaging. Unfortunately, as illustrated in FIG. 16, such long working distances in an ESE microscope dramatically degrade the quality of a image. As shown in FIG. 17, however, by "wetting" the sample with a liquid prior to imaging, image quality is significantly improved. Apparently, the wetting of the sample causes an increase in image strength. Moreover, wetting the sample allows the chamber pressure to be reduced, which decreases the amount of water vapor between the sample and the detector. The moisture for imaging is provided to some extent, by moisture evaporating off the sample itself. Samples which were difficult to image over 500× magnification prior to treatment can be viewed with better image quality at magnifications of 1000× or better. If it is desirable to improve image quality without dissolving the sample, a liquid could be used in which the sample is not soluble. Water vapor, however, is expected to produce the best signal quality increase.

EXAMPLE 2

Figure 20:
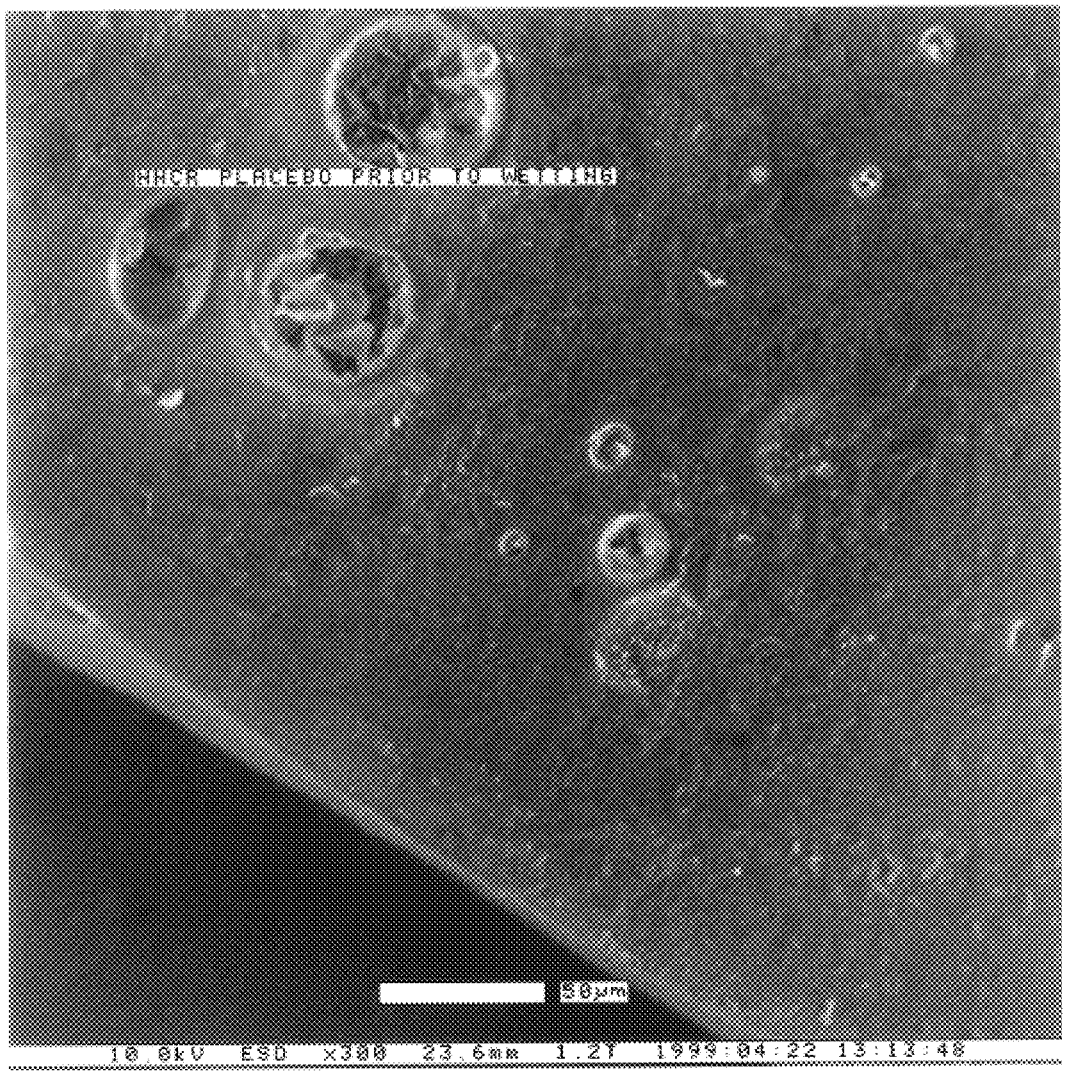
FIG. 20 is a photograph of an unmoistened sample imaged at 300×(comparative).
Figure 21:
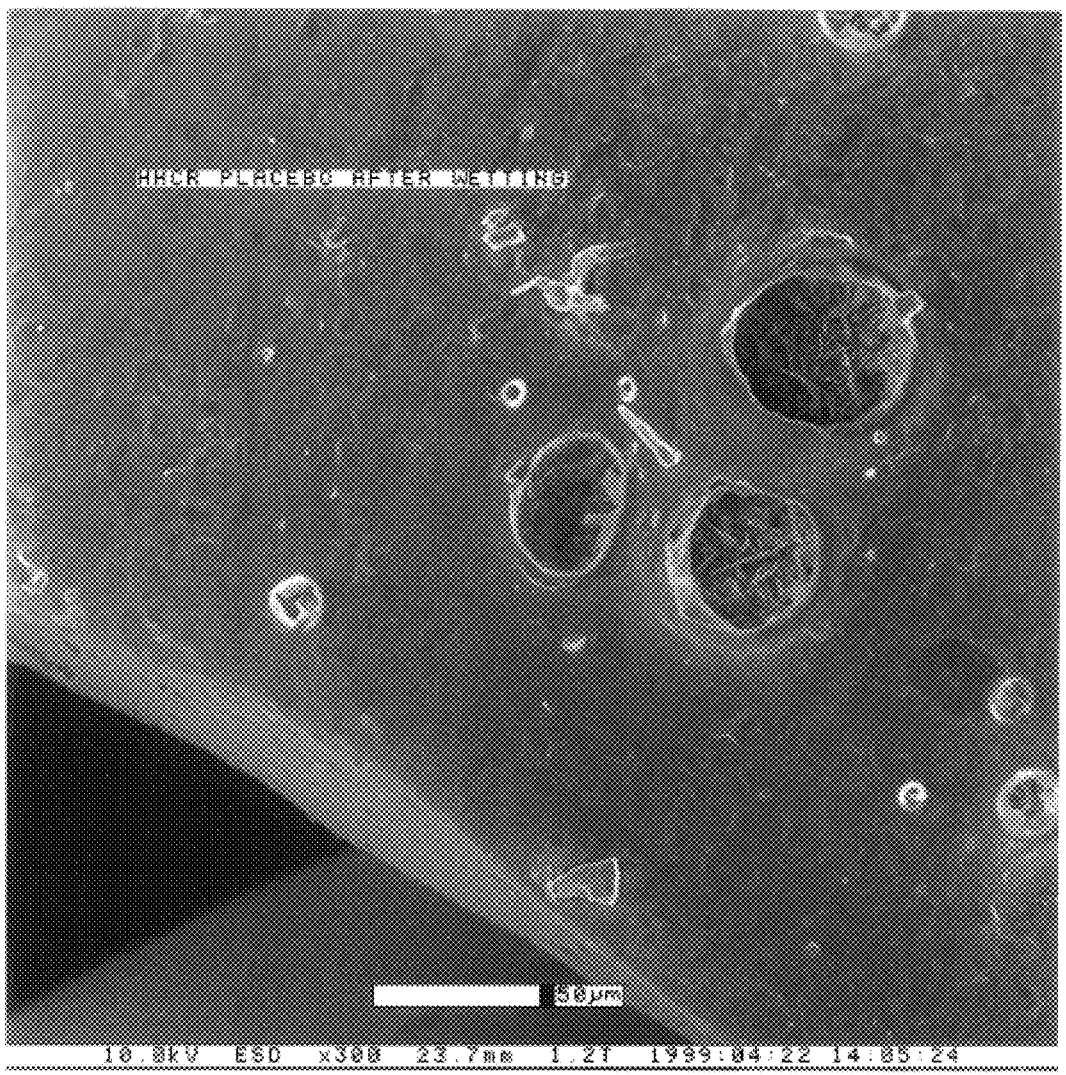
FIG. 21 is a photograph of the sample of FIG. 20 after being immersed in a dissolution bath for 15 minutes and imaged at 300×.

A placebo melt extruded pellet was mounted with the aid of mounting cement to a mounting stub, and the mounting stub and pellet were placed in a dissolution stage in accordance with FIGS. 3–12. The ESE microscope and associated controllers are identical to the components of Example 1, except that the VCR is replaced with a computer configured to store images from the ESE microscope. The placebo pellet was imaged with the following parameters: magnification, 300×, chamber pressure 1.2 Torr, accelerating voltage 10 Kv. The resultant image is shown in FIG. 20. Then, the ESE microscope chamber was vented and dissolution of the pellet was conducted in accordance with the present invention for 15 minutes at a flow rate of 40 ml/min through the sample well 210 with recirculating deionized water. The stage was then drained and the sample imaged with the same parameters as described above to generate FIG. 21. FIGS. 20 and 21 are images of the same pellet at the same position. However, a comparison of FIGS. 20 and 21 illustrate that the wetted sample (FIG. 21) generated a higher quality image than the dry sample (FIG. 20). For example, it is apparent that the details and topography are better pronounced, and the edges of the pellet better defined in FIG. 21.

Wetting of a sample allows excess electrical charge buildup to be conducted off the sample surface. This also improves imaging quality. By decreasing the negative charge on the sample surface, the amount that the imaging beam is deflected is reduced. Image resolution and quality is thereby improved.

EXAMPLE 3

Figure 22:
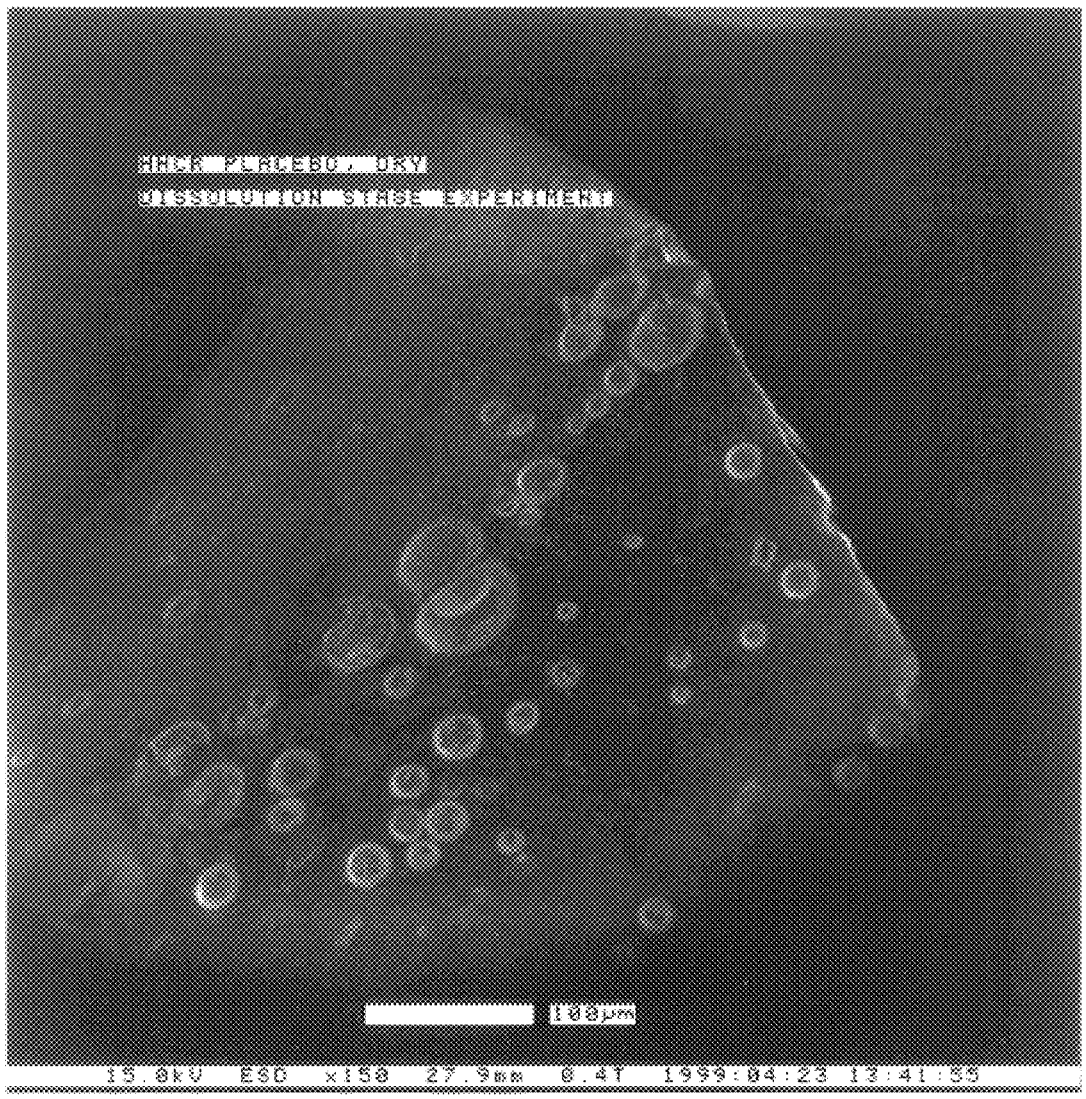
FIG. 22 is a photograph of an unmoistened sample imaged at 0.4 Torr chamber pressure and 150×(comparative)

A melt extruded placebo pellet was mounted with the aid of mounting cement to a mounting stub, and the mounting stub and pellet were placed in a dissolution stage in accordance with FIGS. 3–12. The ESE microscope and associated controllers are identical to the components of Example 1, except that the VCR is replaced with a computer configured to store images from the ESE microscope. The placebo pellet was imaged with the following parameters: magnification 150×, chamber pressure 0.4 Torr; accelerating voltage 15 kV. The resultant image is shown in FIG. 22. Then, the ESE microscope chamber was vented and dissolution of the pellet was conducted in accordance with the present invention for 15 minutes at a flow rate of 40 ml/min through the sample well 210 with recirculating deionized water. The stage was then drained and the sample imaged with the same parameters as described above to generate FIG. 23.

Figure 23:
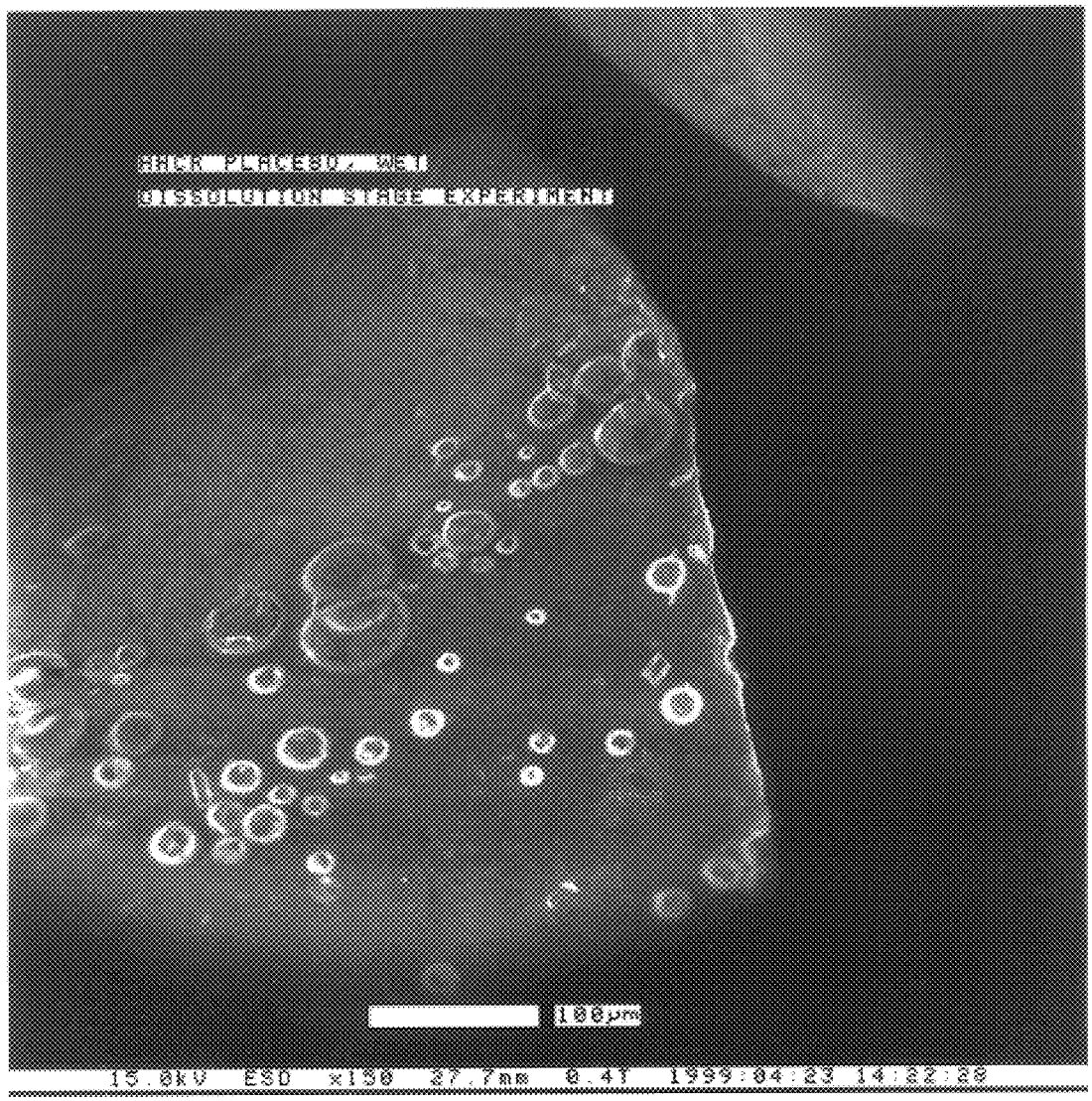
FIG. 23 is a photograph of the sample of FIG. 22 after being immersed in a dissolution bath for 15 minutes and imaged at 0.4 Torr chamber pressure and 150×.

The images of FIGS. 22 and 23 were generated at a reduced chamber pressure (0.4 Torr) as compared to chamber pressure (1.2 Torr) of the images of FIGS. 20 and 21. Imaging at a reduced chamber pressure reduces beam interference from gas molecules, but also decreases the signal, resulting in dim, poor quality images. However, wetting a sample prior to imaging restores the signal, increasing the image quality without the beam interference associated with higher chamber pressures. The image of the unwetted sample (FIG. 22) appears "washed out" at 0.4 Torr, whereas the image of the wetted sample (FIG. 23) exhibits improved contrast and resolution.

EXAMPLE 4

Figure 24A:
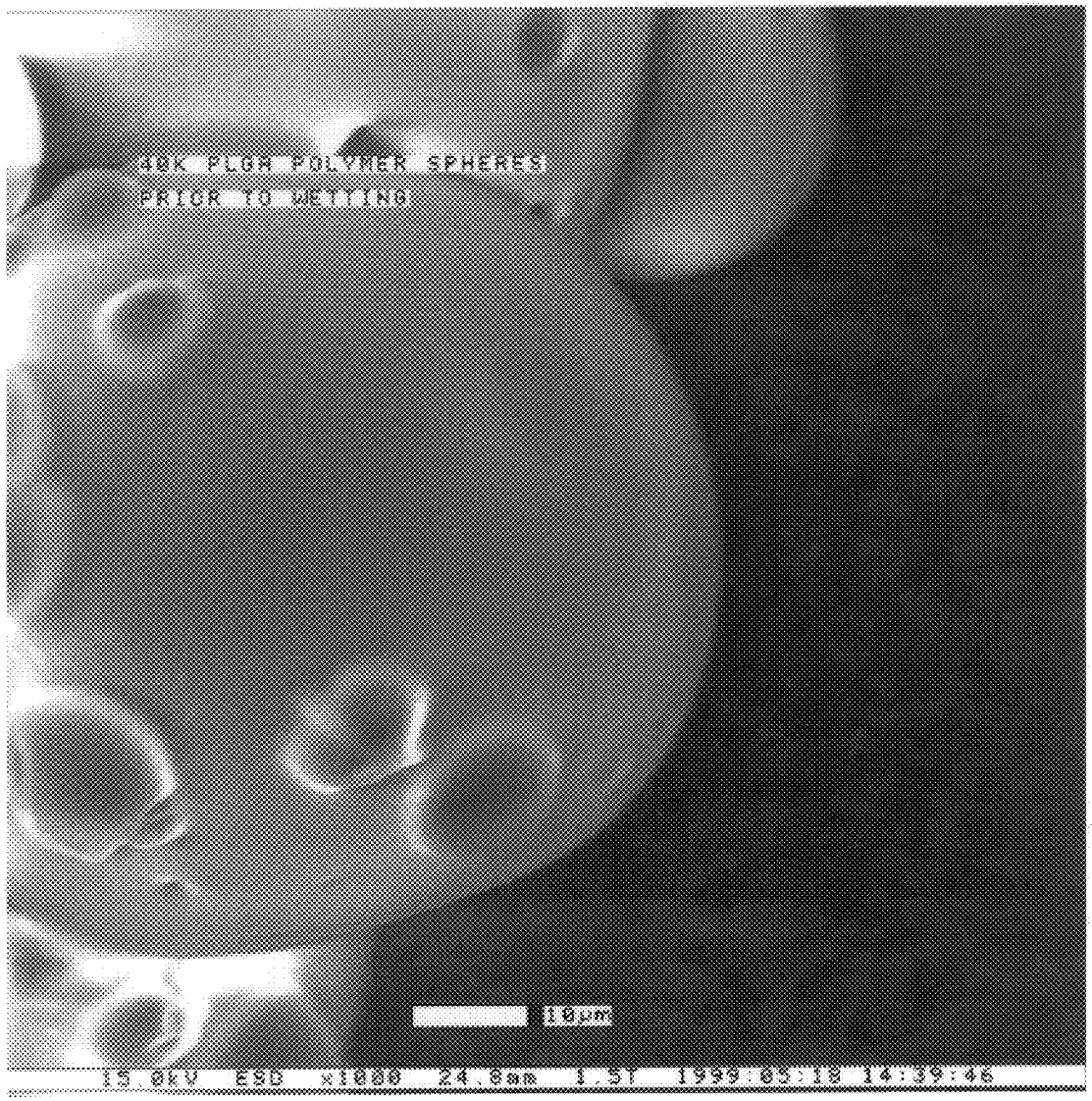
FIG. 24a is a photograph of an unmoistened sample imaged at 1000×.
Figure 24B:
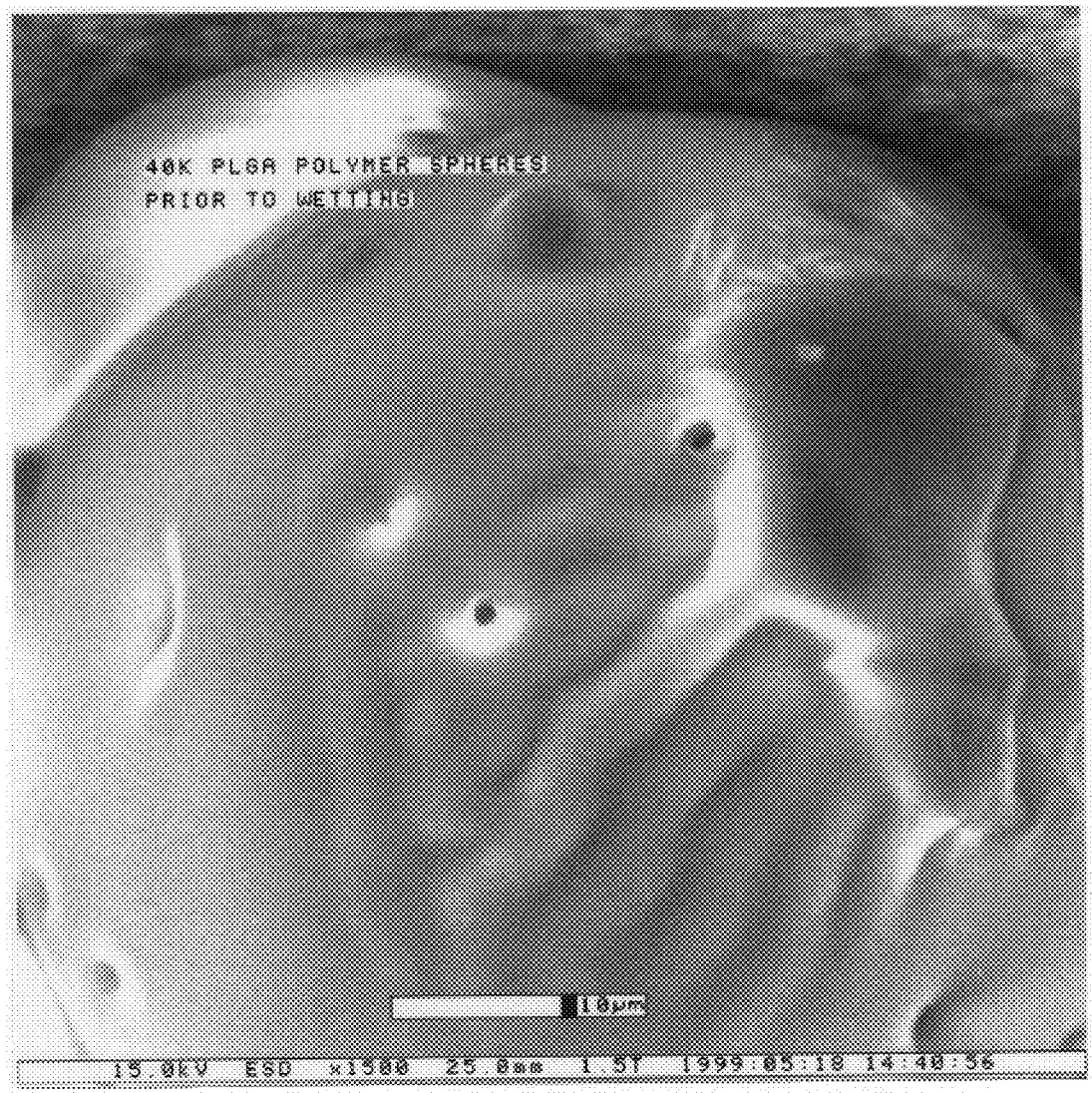
FIG. 24B is a photograph of an unmoistened sample imaged at 1500×.
Figure 24C:
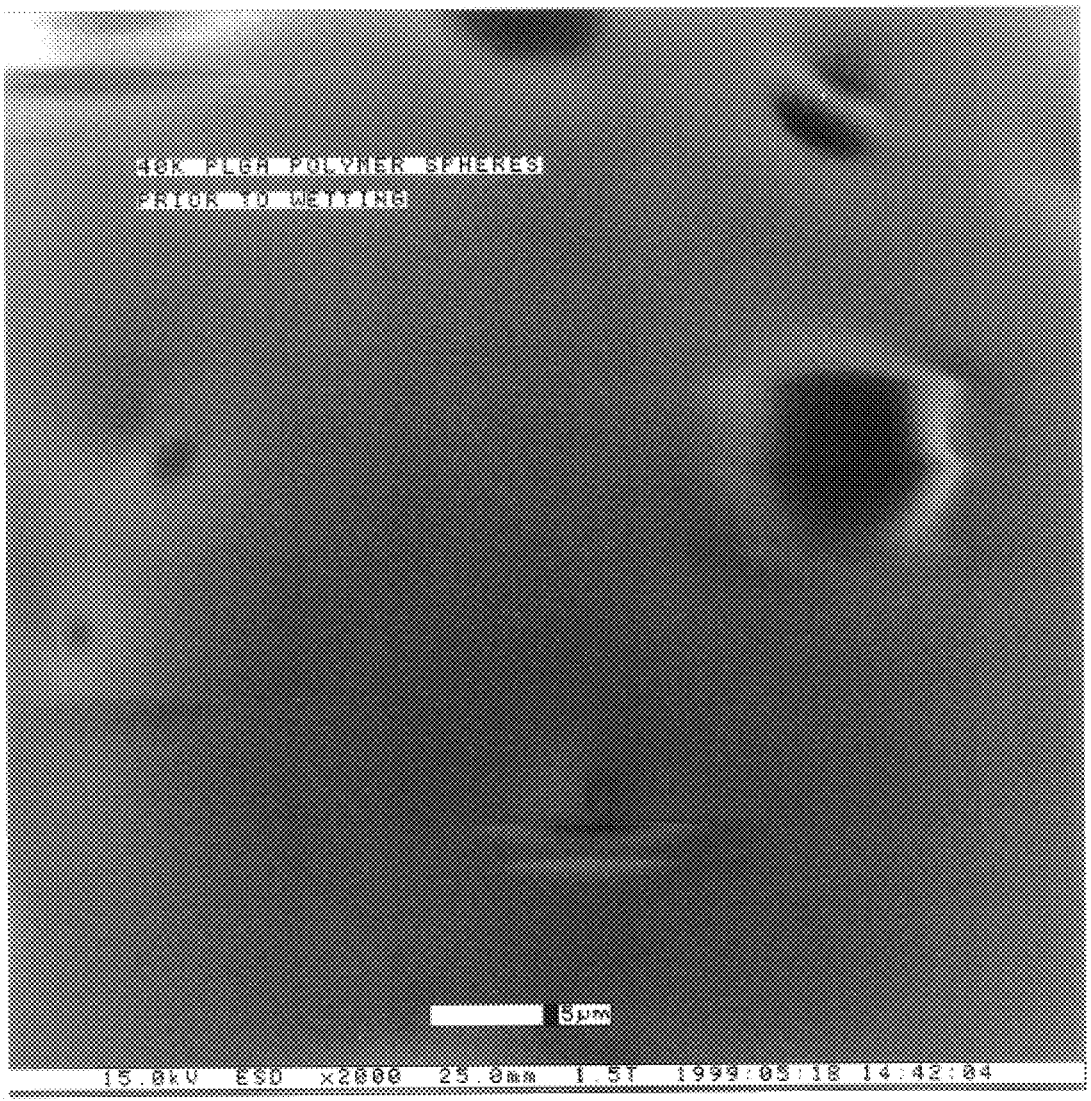
FIG. 24C is a photograph of the sample of FIG. 24a imaged at 2000×.

Polymer microspheres were mounted with the aid of an adhesive tape to a mounting stub, and the mounting stub and microspheres were placed in a dissolution stage in accordance with FIGS. 3–12. The ESE microscope and associated controllers are identical to the components of Example 1, except that the VCR is replaced with a computer configured to store images from the ESE microscope. The microspheres were imaged with the following parameters: chamber pressure 1.5 Torr, accelerating voltage 15.0 kV, and magnification 1000× (FIG. 24a), 1500× (FIG. 24b) and 2000× (FIG. 24c). Microspheres are very sensitive samples. As illustrated in FIGS. 24a, 24b, and 24c, the polymer surface of the microspheres "bubbled" during imaging, a result of beam damage from imaging at 1000×, 1500×, and 2000×. The beam damage is particularly pronounced in FIG. 24b.

Figure 25A:
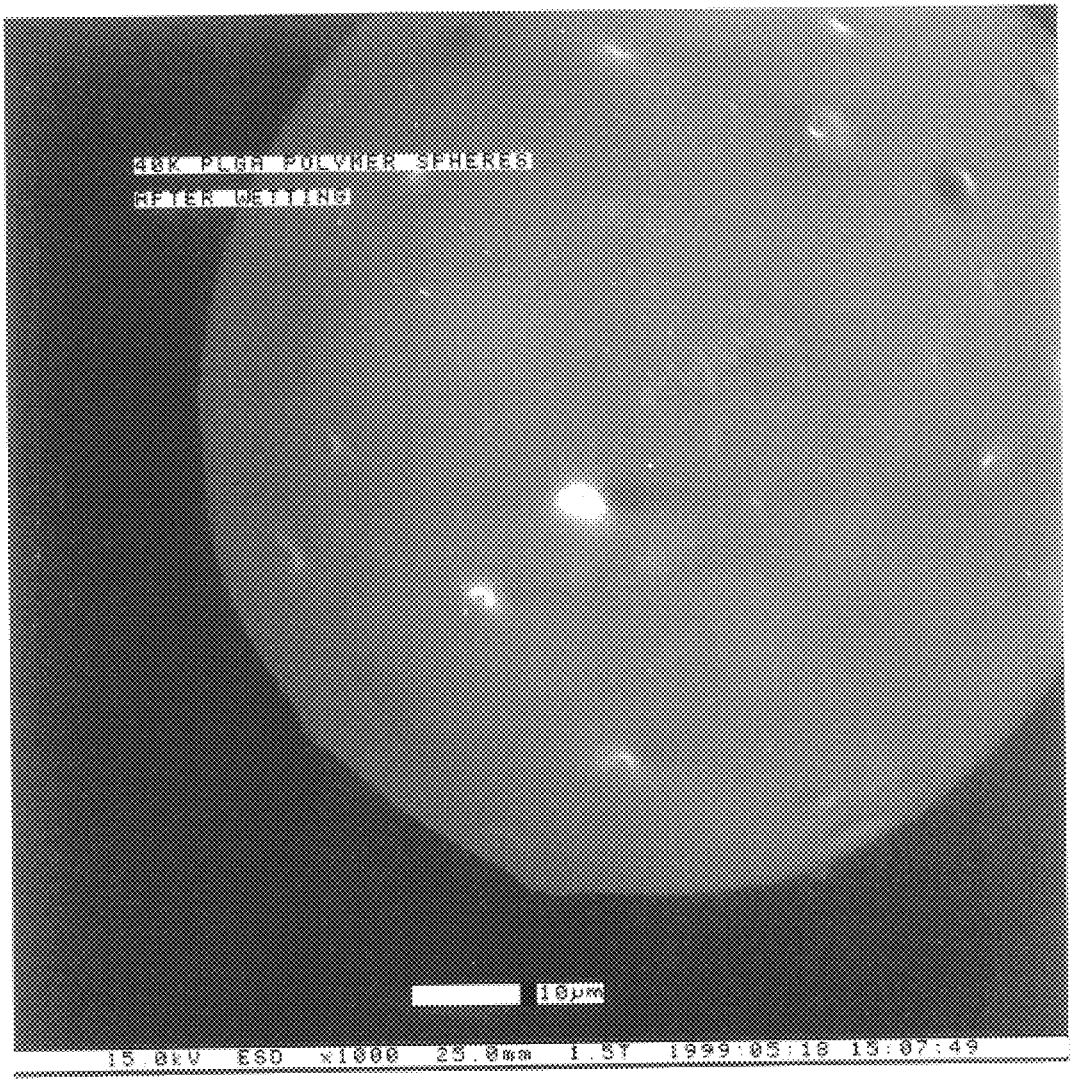
FIG. 25a is a photograph of a sample after being immersed in a dissolution bath for 15 minutes and imaged at 1000×.
Figure 25B:
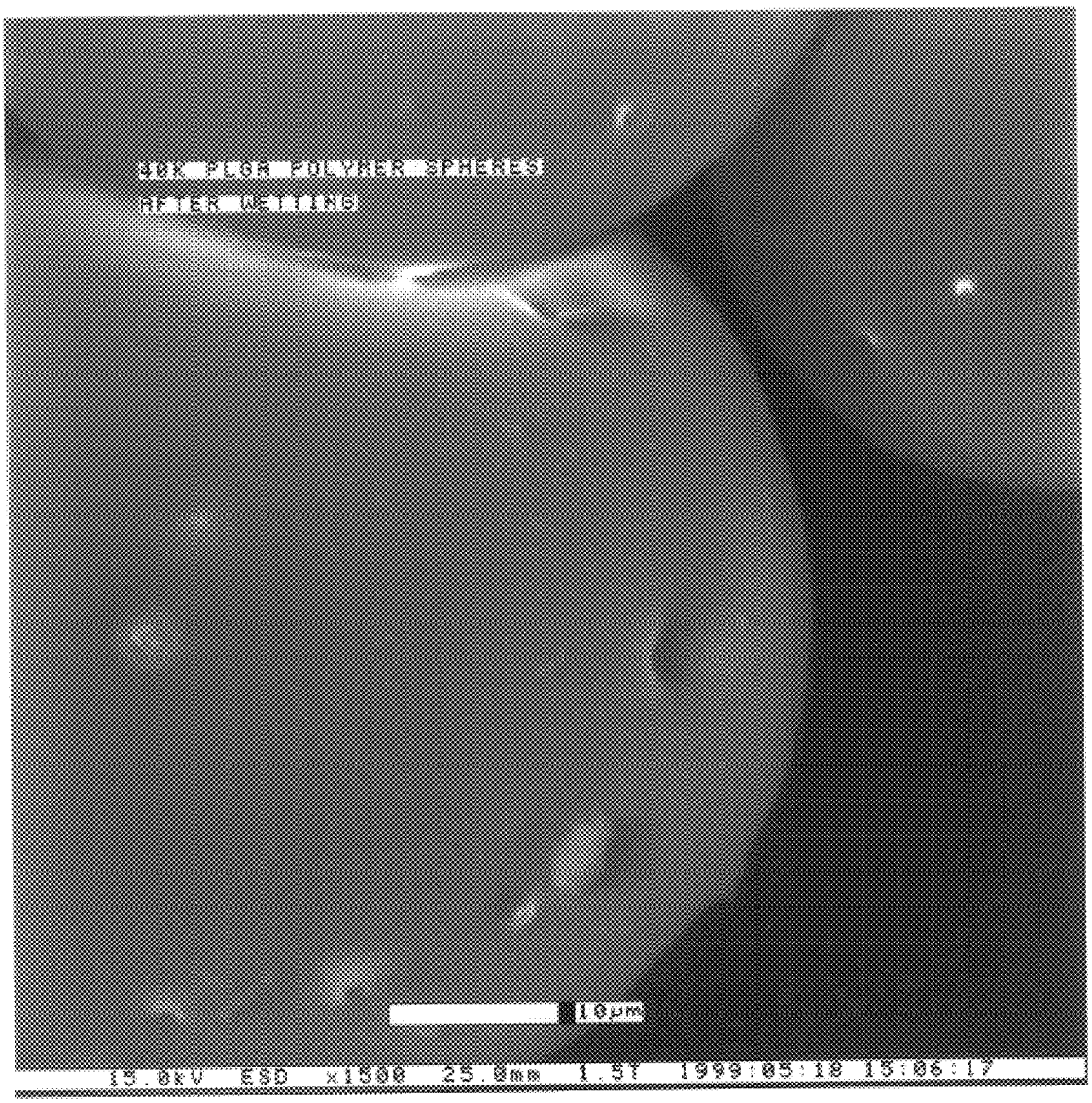
FIG. 25b is a photograph of the sample of FIG. 25a imaged at 1500×.
Figure 25C:
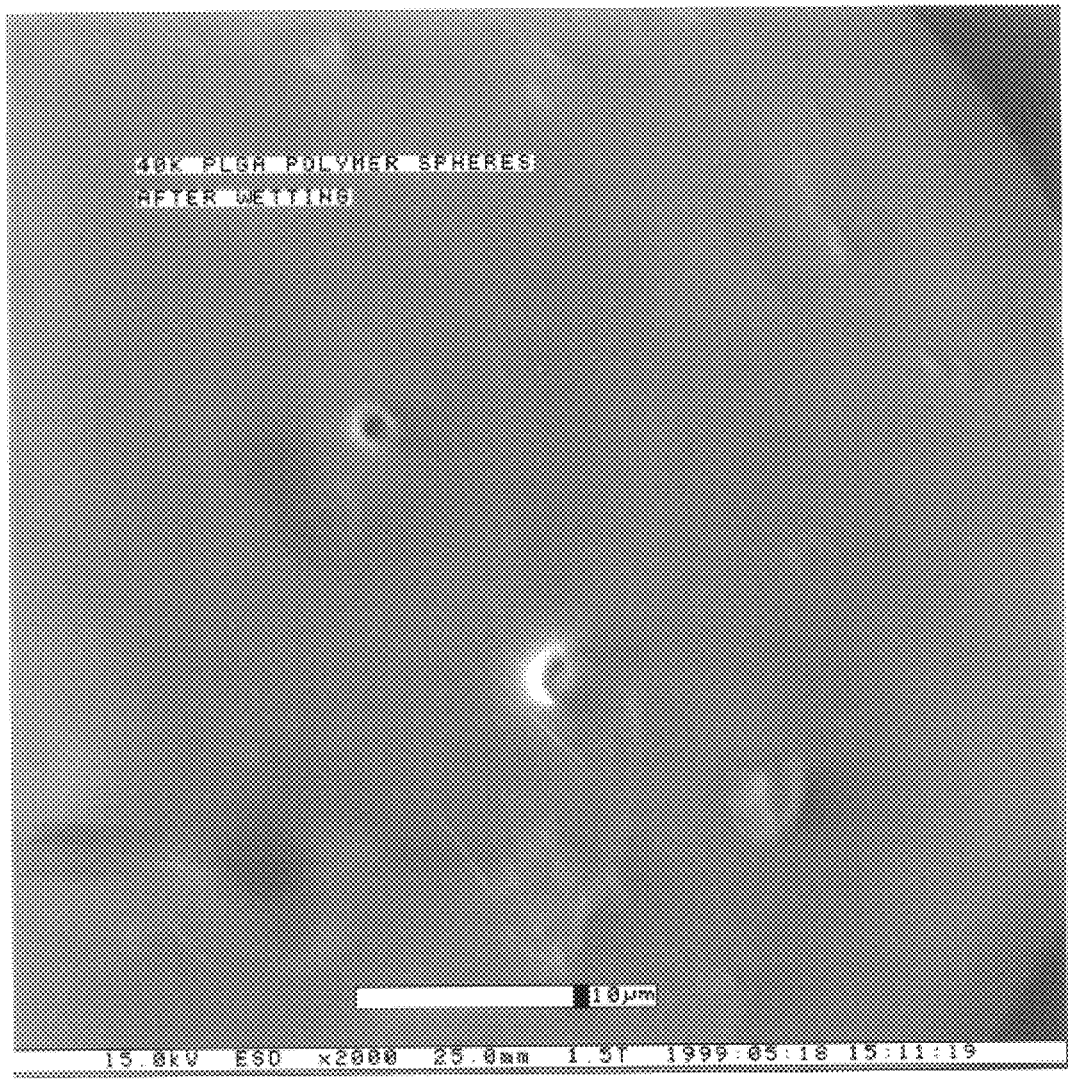
FIG. 25c is a photograph of the sample of FIG. 25a imaged at 2000×.

Polymer microspheres of the same composition were mounted in the same manner, and the ESE microscope chamber was vented and dissolution of the microspheres was conducted in accordance with the present invention for 15 minutes at a flow rate of 40 ml/min through the sample well 210 with recirculating deionized water. The stage was then drained and the sample imaged with the same parameters as described above to generate FIGS. 25(a) (1000×), 25(b) (1500×), and 25(c) (2000×). As compared to unwetted microsphere of FIG. 24a, the wetted microsphere of FIG. 25a does not exhibit beam damage at 1000×. Similarly, even at 1500× or 2000×, the wetted sample does not exhibit beam damage, as evidenced by the lack of bubbling.

During the experiments of Examples 2 through 4, the sample well of the sample chamber of FIGS. 2 through 12 was not covered with a lid. For this reason, the ESE microscope was vented prior to the beginning of the dissolution cycle. However, in accordance with the embodiment of the invention which utilized a movable lid 400, there is no need to vent the ESE microscope prior to the dissolution cycle.

EXAMPLE 5

Automated Downstream Processing

As set forth above, recirculating the dissolution fluid also provides the advantage of allowing the user to monitor samples of the dissolution fluid from the SDF 150 at various stages of a dissolution experiment in order to analyze the substances which have been dissolved into the fluid (such as drugs, diluents, etc.). In this regard, for example, the dissolution of an active agent (or other component) of a sample can be monitored over time utilizing a dissolution stage in accordance with the invention.

For example, the dissolution of an active agent from a tablet can be monitored in real time as the tablet undergoes dissolution in the sample chamber in the ESE microscope. Periodically, the sample well of the sample chamber can be drained, and the tablet imaged in the ESE microscope.

To demonstrate this feature, a dissolution vessel containing 900 ml of water was used as the SDF 150. Two peristaltic pumps were used to circulate the dissolution medium (filtered deionized water) through the sample well. One pump is set to deliver water to the sample well (through port 50) at 30 ml/min and the other pump withdraws the water from the sample well through port 51 (adjusted to 40 ml/min to prevent overflow). The temperature in the vessel was maintained at 37° C. using a thermostat-controlled water bath.

Dissolution of an active agent was measured using an Ocean Optics UV-optimized spectrometer (model S1000). The spectrometer was controlled through an Excel spreadsheet running on a Texas Micro workstation. The workstation was equipped with a 133 MHz Pentium processor and 128 kb of RAM.

A flow-through UV cell was used to collect ultraviolet spectral data from the dissolution vessel at specified times, using fiber-optic cables to pass the radiation through the cell. A flow diverter draws fluid from the dissolution vessel through the cell and join this with additional flow from another input tube inserted into the dissolution vessel.

Figure 26:
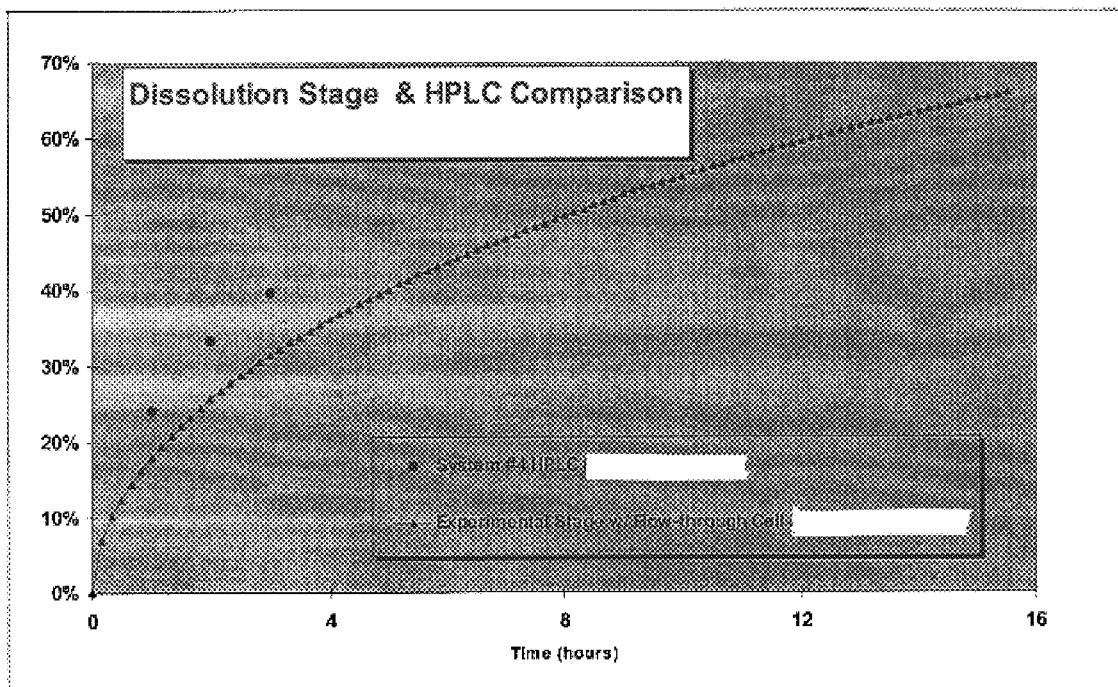
FIG. 26 is a plot of percent tramadol dissolved from a controlled release tramadol tablet versus time during dissolution of said tablet over 16 hours in the sample chamber of FIGS. 3 through 12, and of percent tramadol dissolved from a controlled release tramadol tablet verus time during dissolution of the tablet over 24 hours using a prior art HPLC method.

A 200 mg controlled release tramadol tablet was placed freely into the sample well. Tramadol can be detected by its absorption at a wavelength of 272 nm, correcting for the background signal by subtracting the absorption at 300 nm. The dissolution system was used to obtain release profiles from a Tramadol tablet (200 mg), by circulating the dissolution fluid from the dissolution vessel through the sample well, and sampling the dissolution media with the flow cell in real time every 10 minutes. The measured concentration was calibrated against a raw material standard. The results are shown in FIG. 26. FIG. 26 also shows the release profile of a 200 mg controlled release tramadol tablet, as measured by a prior art high pressure liquid chromatography (HPLC) method. The dissolution results obtained with the flow cell are roughly comparable to those obtained from tramadol tablets by the standard HPLC dissolution method. This demonstrates that the downstream processing system in accordance with the present invention can provide reliable and accurate dissolution results while, at the same time, providing ESE microscope images of the sample at selected times during dissolution.

Alternative instruments could also be used to measure the amount of analyte in the dissolution media. For example, a fiber optic UV probe, such as the probe described in WO 97/46860, entitled IMPROVEMENTS IN DETECTION SYSTEMS AND METHODS FOR PREDICTING THE DISSOLUTION CURVE OF A DRUG FROM A PHARMACEUTICAL DOSAGE FORM, the entire disclosure of which is hereby incorporated by reference, could be disposed within the dissolution vessel. It is anticipated, however, that it may be necessary to modify the probe, or to provide an additional structure or mechanism to prevent air bubbles from forming in the aperture of the probe. For example, the UV probe could be mounted directly in line with the pump tubing using a mounting block, or be situated in front of the pump line drawing fluid from the dissolution beaker, so that air bubbles are forced through by the flow of liquid.

In accordance with another embodiment of the invention, a single peristaltic pump could be used instead of two peristaltic pumps, and the outgoing fluid from the flow cell could be returned to a separate vessel instead of directing it back to the dissolution vessel.

In accordance with other embodiments of the invention, other or additional downstream processing devices could be employed, such as an autosampler, or other types of detection systems. Moreover, other types of dissolution media, or alternative types of microscopy could be employed.

For example, an autosampler could be used to withdraw samples from the dissolution vessel at specified times which could be examined by chromatographic methods or other analytical techniques. Other detector types for chemical analysis could be easily connected to the system; which would include near infrared, conductivity, optical rotation, or refractive index detection. The imaging performed on the dissolving sample could be modified (for example) to use light microscopy, near infrared microscopy, or polarized light microscopy. Moreover, alternative dissolution media could be used, including simulated gastric fluid (SGF) or simulated intestinal fluid SIF, provided that materials were used for the sample chamber, and associated components, which would not be damaged or corroded by the dissolution media used.

What is claimed is:

1. A system for imaging a sample in a variable pressure microscope, comprising:
    a variable pressure microscope having a specimen chamber for imaging a sample;
    a source of dissolution fluid;
    a dissolution fluid drain;
    a sample chamber, disposed in the specimen chamber, the sample chamber having a sample well, a first fluid port, and a second fluid port, the first and second fluid ports being coupled to the sample well, the first fluid port being further coupled to the source of dissolution fluid, and the second fluid port being further coupled to the dissolution fluid drain.

2. The system according to claim 1, wherein the sample well includes a first aperture into which the first fluid port opens and a second aperture into which the second fluid port opens, the first aperture being closer to a bottom of the well than the second aperture.

3. The system according to claim 2, further comprising a vacuum generator, the vacuum generator and the source of dissolution fluid being selectively coupled to the first fluid port.

4. The system according to claim 3, wherein the dissolution fluid drain is coupled to the source of dissolution fluid to recirculate the dissolution fluid.

5. The system according to claim 3, further comprising a controller coupled to the source of dissolution fluid and the vacuum generator, the controller being operable to selectively couple the source of dissolution fluid to the first fluid port in order to fill the sample well with dissolution fluid during a dissolution cycle of the variable pressure microscope, and to selectively couple the vacuum generator to drain the dissolution fluid from the sample well prior to an imaging cycle of the variable pressure microscope.

6. The system according to claim 1, wherein the sample chamber includes a third fluid port coupled to a source of temperature controlled fluid, the third fluid port being coupled to a passage which at least partially surrounds the sample well, the passage being coupled to a temperature controlled fluid drain.

7. The system according to claim 6, wherein the sample chamber includes a base portion having a cavity formed therein, and a sample well portion having the sample well formed therein, the cavity having a depth and width which is larger than the depth and width of the sample well, the sample well portion having a width which is at least as large as the width of the cavity, the sample well portion being secured over the base portion such that the sample well portion extends contiguously over the cavity and the sample well extends into the cavity, thereby defining the passage.

8. The system according to claim 6, wherein the temperature controlled fluid drain is coupled to the source of source of temperature controlled fluid to recirculate the temperature controlled fluid.

9. The system according to claim 1, wherein the sample chamber further includes a sample well lid for covering the sample well.

10. The system according to claim 9, further including a motor for selectively moving the lid between a closed position and an open position.

11. The system according to claim 1, further comprising a controller coupled to the source of dissolution fluid, the controller being operable to actuate the source of dissolution fluid in order to fill the sample well with dissolution fluid during a dissolution cycle of the variable pressure microscope, and to drain the dissolution fluid from the sample well prior to an imaging cycle of the variable pressure microscope.

12. The system according to claim 1, wherein the variable pressure microscope is an environmental scanning electron microscope.

13. The system according to claim 1, wherein the dissolution fluid is water.

14. The system according to claim 1, wherein the dissolution fluid is simulated gastric fluid.

15. The system according to claim 1, wherein the dissolution fluid is simulated intestine fluid.

16. A method for monitoring the dissolution of a sample in a specimen chamber of a variable pressure microscope, comprising the steps of
    a. placing a sample into a sample well of a sample chamber which is disposed within the specimen chamber of the variable pressure microscope;
    b. creating a flowing dissolution bath in the sample chamber during a dissolution cycle by continuously inputting dissolution fluid into the sample well and continuously draining the dissolution fluid from the sample well, while the sample well remains in the specimen chamber;

c. draining the dissolution fluid from the sample well during a draining cycle, while the sample well remains in the specimen chamber;

d. imaging the sample with the variable pressure microscope;

e. storing the image obtained in step d in an image storage device; and f. automatically repeating steps a through e at preselected time intervals to obtain a plurality of images of the sample.

17. The method according to claim 16, wherein step b further comprises the step of moving a sample well lid to cover the sample well prior to creating said dissolution bath, and wherein step d further comprises the step of moving the sample well lid to uncover the sample well prior to imaging the sample.

18. The method according to claim 16 wherein the sample is an oral solid dosage form of a pharmaceutical having a weight between 100 and 1000 mg.

19. A sample chamber for use with a variable pressure microscope, comprising a sample well, a first fluid port, and a second fluid port, the first and second fluid ports being coupled to the sample well, the first fluid port being for coupling to a source of dissolution fluid, and the second fluid port for coupling to the dissolution fluid drain.

20. The sample chamber according to claim 19, further comprising a sample well lid, the sample well lid being slidingly engaged to the sample chamber to selectively cover and expose the sample well.

21. A method for monitoring the dissolution of a sample in a specimen chamber of a variable pressure microscope, comprising the steps of a. placing a sample into a sample well of a sample chamber which is disposed within the specimen chamber of the variable pressure microscope;

b. creating a flowing dissolution bath in the sample chamber during a dissolution cycle by circulating a dissolution fluid into the sample well from a vessel, while the sample well remains in the specimen chamber;

c. draining the dissolution fluid from the sample well during a draining cycle, while the sample well remains in the specimen chamber;

d. imaging the sample with the variable pressure microscope;

e. storing the image obtained in step d in an image storage device;

f. detecting, from the vessel, an amount of a substance in said dissolution fluid; and g. automatically repeating steps a through f at preselected time intervals to obtain a plurality of images of the sample and a corresponding plurality of amounts of said substance.

22. The method according to claim 21, wherein step b further comprises the step of moving a sample well lid to cover the sample well prior to creating said dissolution bath, and wherein step d further comprises the step of moving the sample well lid to uncover the sample well prior to imaging the sample.

23. The method according to claim 21 wherein the sample is an oral solid dosage form of a pharmaceutical having a weight between 100 mg and 1000 mg.

* * * * *